(12) United States Patent
Colli et al.

(10) Patent No.: US 11,590,145 B2
(45) Date of Patent: Feb. 28, 2023

(54) VAGINAL COMPOSITION COMPRISING A COMBINATION OF ESTROGEN AND VITAMIN D

(71) Applicant: CHEMO RESEARCH S.L., Madrid (ES)

(72) Inventors: Enrico Colli, Madrid (ES); David F. Archer, Norfolk, VA (US)

(73) Assignee: CHEMO RESEARCH S.L., Madrid (ES)

( * ) Notice: Subject to any disclaimer, the term of this patent is extended or adjusted under 35 U.S.C. 154(b) by 0 days.

(21) Appl. No.: 16/952,142

(22) Filed: Nov. 19, 2020

(65) Prior Publication Data

US 2021/0069210 A1 Mar. 11, 2021

Related U.S. Application Data

(63) Continuation of application No. 16/318,510, filed as application No. PCT/EP2017/068391 on Jul. 20, 2017, now abandoned.

(30) Foreign Application Priority Data

Jul. 22, 2016 (EP) .................................... 16305941

(51) Int. Cl.
*A61K 31/565* (2006.01)
*A61K 9/00* (2006.01)
(Continued)

(52) U.S. Cl.
CPC .......... *A61K 31/565* (2013.01); *A61K 9/0034* (2013.01); *A61K 9/0036* (2013.01); *A61K 9/02* (2013.01); *A61K 31/065* (2013.01); *A61K 31/59* (2013.01); *A61K 31/593* (2013.01); *A61K 47/14* (2013.01); *A61P 15/02* (2018.01)

(58) Field of Classification Search
None
See application file for complete search history.

(56) References Cited

U.S. PATENT DOCUMENTS

| | | | |
|---|---|---|---|
| 3,062,715 A | 11/1962 | Reese | |
| 5,204,108 A | 4/1993 | Illum | |

(Continued)

FOREIGN PATENT DOCUMENTS

| | | |
|---|---|---|
| CN | 102641548 A | 8/2012 |
| EP | 0253607 A1 | 1/1988 |

(Continued)

OTHER PUBLICATIONS

Parastou et al., "The effects of vitamin D on vaginal atrophy in postmenopausal women", Iranian Journal of Nursing and Midwifery Research, 2015, vol. 20, No. 2, Mar. 2015, pp. 211-215. (Year: 2015).*

(Continued)

*Primary Examiner* — Kyung S Chang
(74) *Attorney, Agent, or Firm* — WCF IP

(57) ABSTRACT

The invention relates to vaginal composition comprising a combination of estrogen and vitamin D or a vitamin D analog at a daily dosage delivery of (i) estrogen ranging from 1 μg to 100 μg estrogen of estradiol equivalent and (ii) vitamin D or analog ranging from 7.5 μg to 100 μg of vitamin D equivalent.

18 Claims, 9 Drawing Sheets

(51) Int. Cl.

| | |
|---|---|
| *A61K 9/02* | (2006.01) |
| *A61K 31/065* | (2006.01) |
| *A61K 31/59* | (2006.01) |
| *A61K 31/593* | (2006.01) |
| *A61K 47/14* | (2017.01) |
| *A61P 15/02* | (2006.01) |

(56) References Cited

U.S. PATENT DOCUMENTS

| | | | |
|---|---|---|---|
| 5,514,698 | A | 5/1996 | Ahmad et al. |
| 5,989,581 | A | 11/1999 | Groenewegen |
| 6,086,908 | A | 7/2000 | Goepferich |
| 6,086,909 | A | 7/2000 | Harrison et al. |
| 6,855,703 | B1 * | 2/2005 | Hill ............... A61K 31/565 514/170 |
| 7,004,171 | B2 | 2/2006 | Benita et al. |
| 2004/0043071 | A1 | 3/2004 | Pauletti |
| 2005/0070501 | A1 | 3/2005 | Neurath et al. |
| 2005/0276836 | A1 | 12/2005 | Wilson |
| 2008/0193428 | A1 | 8/2008 | Zhou et al. |
| 2008/0312198 | A1 | 12/2008 | Rodriguez |
| 2011/0159091 | A1 | 6/2011 | Stone |
| 2013/0269706 | A1 | 10/2013 | Tsao |
| 2015/0328319 | A1 | 11/2015 | Chen et al. |
| 2017/0014458 | A1 | 1/2017 | Thoral et al. |

FOREIGN PATENT DOCUMENTS

| | | | | |
|---|---|---|---|---|
| EP | 0889724 | A1 | | 1/1999 |
| EP | 0900564 | A1 | | 3/1999 |
| EP | 2366395 | A1 * | | 9/2011 ............. A61P 43/00 |
| EP | 2799042 | A1 | | 11/2014 |
| EP | 2849735 | A1 | | 3/2015 |
| JP | 3705620 | B2 | | 10/2005 |
| WO | 0061123 | A2 | | 10/2000 |
| WO | 2002047692 | A1 | | 6/2002 |
| WO | 2004067063 | A2 | | 8/2004 |
| WO | 2004103232 | A1 | | 12/2004 |
| WO | 2005016321 | A1 | | 2/2005 |
| WO | 2006023496 | A2 | | 3/2006 |
| WO | 2007089733 | A1 | | 8/2007 |
| WO | 2011011099 | A1 | | 1/2011 |
| WO | 2013098591 | A1 | | 7/2013 |
| WO | 20150135915 | A1 | | 9/2015 |
| WO | 2016054002 | A1 | | 4/2016 |

OTHER PUBLICATIONS

MacBride et al., "Vulvovaginal Atrophy", Mayo Clin Proc., Jan. 2010; 85(1), pp. 87-94 (Year: 2010).*
Mc Bride M et al., 2010 "Vulvovaginal atrophy". Mayo Clin Proc ; 85 (I):87-94.
NAMS, 2010, "Contemporary Clinical Management of Menopause".
Sturdee DW et al., 2010. Climacteric: 1-24.
NAMS, 2013, "Management of symptomatic vulvovaginal atrophy: 2013 Position statement of the North American Menopause Society". Menopause, 20 ;(9):888.
Johnston SL, Farrell SA, Bouchard C et al. The detection and management of vaginal atrophy. J. Obstet. Gynaecol. Can. 26, 503-515 (2004).
Furness S et al., "Hormone therapy in postmenopausal women and risk of endometrial hyperplasia ". Cochrane database Syst Rev 2009/CD000402.
Suckling J. et al, 2006, Cochrane Database Syst Rev. Oct. 18;(4):CD00150.
Labrie F et al, 2009, Menopause, Jan-Feb;16(I):30-6.
Bachmann G. et al, 2008, Obstet Gynecol. Jan;I I(I):67-76.
Panay N et al., 2012. Menopause; 18(1): 15-9.
Chollet JA., 2011, Patient preference and adherence;5:571-574.
Yildirim B et al, 2004, Maturitas Dec. 10;49(4):334-7.
Rad P et al., 2015, Iran J Nurs Midwifery Res., Mar-Apr;20(2):211-5.
Leblanc E et al, Maturitas. Jul. 2015;81(3):377-83.
Checa MA et al.,. Maturitas. Sep. 16, 2005;52(I):70-7.
Zeyneloglu HB et al, Fertil Steril. Aug. 2007;88(2):530-2.
Schulte-Uebbing C et al., Dermatoendocrinol. Apr. 19, 2016;8(I):eI079359.
EFSA Journal 2012;10(7):2813.
Skowronski et al. (1995) Endocrynology 136(1): 20-26.
Unkila M et al, J Steroid Biochem Mol Biol. Nov. 2013;138:107-15.
Berger L et al., J Steroid Biochem Mol Biol. Mar. 2008;109(I-2):67-80.
Berger L et al, J Steroid Biochem Mol Biol. Jul. 2005;96(2):201-15).
Montoya TI et al, 2015; Biol Reprod.;92(2):43.

* cited by examiner

VAGINAL COMPOSITION COMPRISING A COMBINATION OF ESTROGEN AND VITAMIN D

FIELD OF THE INVENTION

The present invention relates to the field of treating vaginal atrophy.

BACKGROUND OF THE INVENTION

Women experienced many physical changes during the period of menopause transition and after menopause including vasomotor symptoms (hot flashes, night sweats), sleep disturbance, mood changes and also vulvovaginal symptoms, urinary incontinence and osteoporosis. All of these symptoms or related health conditions are caused by a decrease in estrogens and other hormones and the effects of aging.

Vulvovaginal symptoms include vaginal dryness, vulvovaginal irritation/itching, and dyspareunia, and are experienced by an estimated from about 4% in the early pre-menopausal groups to 47% in the late postmenopausal group (Mc Bride M et al., 2010 "Vulvovaginal atrophy". Mayo Clin Proc; 85 (1):87-94). In contrast to vasomotor symptoms, which usually abate over time even without treatment; symptomatic vaginal atrophy is typically progressive and unlikely to resolve on its own (NAMS, 2010,"Contemporary Clinical Management of Menopause"). Vulvovaginal atrophy (VVA) is characterized by different physical signs. The mucosa of the cervix, the epithelium of the vagina and vulva thin and become susceptible to injury; the vaginal rugae diminish leading to a smoother appearing vaginal wall which is accompanied by diminished blood flow (Sturdee D W et al., 2010. Climacteric: 1-24). Left untreated, severe vulvovaginal atrophy can result in a vaginal surface that is friable, with petechial, ulcerations and tears, accompanied in some cases by stenosis. Bleeding may occur from minimal trauma: wiping, speculum insertion and also during intercourse (NAMS, 2013, "Management of symptomatic vulvovaginal atrophy: 2013 Position statement of the North American Menopause Society". Menopause, 20;(9):888). Consequently before irreversible changes occur, early detection and treatment of vaginal atrophy should be implemented. Moreover long-term therapy may be necessary to maintain vaginal (urogenital) health.

One of the options for postmenopausal women with symptoms and quality of life issues is to receive hormone replacement therapy (estrogen alone or a combination of estrogens and progestins). While systemic hormone replacement therapy is effective in abating vasomotor-related discomfort, 25% to 40% of women using systemic treatment still experience persistent vaginal dryness (Johnston S L. Farrell S A. Bouchard C et al. The detection and management of vaginal atrophy. J. Obstet. Gynaecol. Can. 26, 503-515 (2004)). Moreover, the systematic administration of unopposed estrogen has been shown to be associated with an increased risk for endometrial hyperplasia and carcinoma in a dose- and duration-dependent manner in postmenopausal women who have not gone hysterectomy (Furness S et al., "Hormone therapy in postmenopausal women and risk of endometrial hyperplasia". Cochrane database Syst Rev 2009/CD000402). Thus, if vasomotor symptom relief or osteoporosis prevention is not indicated, recommended treatment for women experiencing vulvovaginal atrophy is local estrogen application with drugs providing minimal systemic absorption.

Vaginal estrogen products deliver estrogen locally to vaginal tissues with systemic absorption proportional to dose used. Various vaginal estrogen preparations such as conjugated equine estrogens (Premarin®), estradiol (Estrace®) vaginal creams, a sustained-release intra-vaginal estradiol ring (Estring®) and a low-dose estradiol (Vagifem®) and estriol tablets are useful therapeutic options in the treatment of this condition. All treatments provided equivalent relief of the symptoms of VVA based on composite scores of vaginal symptoms (dryness, soreness, and irritation) (Suckling J. et al., 2006, Cochrane Database Syst Rev. Oct 18;(4):CD00150). Although intravaginal formulations were developed to avoid systemic exposure to estrogens, several studies have demonstrated that all vaginal products lead to significant increases in scrum estrogen levels and thus that systemic action is expected (Labrie F et al., 2009, Menopause. January-February; 16(1):30-6).

Safety information, especially regarding long-term exposure associated with local estrogen therapy is not well documented in the literature to support an assumed more favorable risk-benefit ratio for endometrial hyperplasia and carcinoma. Even if it is rare, endometrial hyperplasia has been seen with low-dose vaginal estrogens (Bachmann G. et al., 2008, Obstet Gynecol. January; 111(1):67-76. Suckling J. et al., 2006. Cochrane Database Syst Rev. Oct 18;(4): CD00150). Such risk is not acceptable for patients.

Ultra-low dose of estrogen have been evaluated with the aim to avoid systemic effects and to reduce side effects. For instance, the 10 μg estradiol vaginal tablets Vagifem has been developed to offer the lowest effective hormonal dose (Panay N et al., 2012. Menopause: 18(1):15-9). Even at these dosages, a minor degree of systemic absorption may occur in some patients, especially during the first two weeks of treatment. In an open-label, multicenter trial on 386 women, incidence rate of hyperplasia and/or carcinoma was 0.52% (95% CI 0.06%, 1.86%) at the end of 52 weeks treatment. Improvements on vulvovaginal atrophy are significantly higher than for the placebo but as expected lower than with increased doses (the 25 meg estradiol vaginal tablet for instance) (Chollet J A., 2011, Patient preference and adherence:5:571-574).

Overall, the improvement of symptoms with local estrogen therapy is currently not optimal: as an example, improvement of objective symptoms with Vagifem 25 mcg/day vs placebo has been only 41.4% (Chollet J A., 2011, Patient preference and adherence; 5:571-574).

Several authors have evaluated alternative treatments to avoid estrogen use, especially to overcome potential risk of endometrial hyperplasia and carcinoma. Conflicting reports suggest the use of vitamin D would be beneficial on vaginal atrophy. Yildirim has shown that oral vitamin D supplementation (0,500 meg calcitriol/day) for at least one year in postmenopausal women resulted in squamous maturation of the vaginal epithelium compared to non-supplemented postmenopausal women (Yildirim B et al., 2004. Maturitas Dec 10:49(4):334-7). Similarly, Rad tested the effect of vaginal vitamin D (suppository 1000 IU vit D Rocatrol, daily for 8 weeks) on vaginal atrophy in 44 postmenopausal women and demonstrated a significant increase of superficial cells in the vaginal epithelium and a significant decrease in vaginal pH. (Rad P et al., 2015, Iran J Nurs Midwifery Res., March-April; 20(2):211-5). On the contrary, results from the Women Health Initiative trial suggest that supplementation with 1000 mg of calcium and 400 IU of vitamin D does not influence menopause-related symptoms, including vaginal dryness, over an average of 5.7 years of follow-up among postmenopausal women (Leblanc E et al., Maturitas. 2015

Jul; 81(3):377-83). In osteoporotic women discontinuing estrogen replacement therapy, Checa came to a similar conclusion and demonstrated a significant decrease in vaginal maturation value in the oral calcium (500 mg/day) plus vitamin D3 (400 IU/day) group one after one year of treatment (Checa MA et al., Maturitas. 2005 September 16; 52(1):70-7.) Thus there is no consensus on the effect of vitamin D on vaginal atrophy.

Use of oral combination of estradiol and a combination of vitamin D and calcium is already known in the treatment of osteoporosis. Vitamin D use in this case is clearly intended to regulated calcium homeostasis and bone turnover.

Effect of a combination of oral raloxifene (60 mg/day) in association with 400 IU vitamin D and 600 mg of calcium on vaginal maturation index and urogenital symptoms has been evaluated in postmenopausal osteoporotic women, by Zeyneloglu et al. These authors demonstrated an improvement in the vaginal maturation index and in the vaginal pH after 3 months of a treatment with a raloxifen-based regimen, as compared with a 3 months treatment with a risedronate-based regimen, both regimen comprising a daily administration of 400 UI of vitamin D (Zeyneloglu H B et al., Fertil Steril. 2007 August; 88(2):530-2).

Also, vaginal combination of high dose estriol (0.5 mg) and vitamin D (12500 IU) has been evaluated for the treatment of stress incontinence. The combination administered three times a week for six weeks increased vitamin D serum level and brought a partial improvement on incontinence symptoms to therapy with single estriol. The study was small and not considered representative by the authors. No effect on vaginal epithelium is mentioned. (Schulte-Uebbing C et al., Dermatoendocrinol. 2016 Apr 19; 8(1):e1 079359.

There is a need in the art for further pharmaceutical compositions that are effective and endowed with a high level of safety for preventing or treating vaginal atrophy.

SUMMARY OF THE INVENTION

This invention relates to a vaginal composition comprising a combination of estrogen and vitamin D or a vitamin D analog at a daily dosage delivery of (i) estrogen ranging from 1 µg to 100 µg estrogen of estradiol equivalent and (ii) vitamin D or analog ranging from 7.5 µg to 100 µg of vitamin D equivalent.

In some preferred embodiments, the daily dosage delivery of estrogen ranges from 1 µg to 70 µg.

In some preferred embodiments, the daily dosage delivery of estrogen ranges from 1 µg to 10 µg.

In some embodiments, the said vaginal composition comprises a combination of estradiol and calcitriol at a daily dosage delivery of (i) estradiol ranging from 1 µg to 10 µg and (ii) calcitriol ranging from 0.25 µg to 1 µg.

In some embodiments, the said vaginal composition has a liquid, solid or semi-solid presentation.

In some embodiments, the said vaginal composition is a cream or a gel composition.

In some embodiments, the said vaginal composition is presented as daily unit dosage form selected in a group comprising a capsule, an ovule, a tablet and a suppository.

In some embodiments, the said vaginal composition is comprised in a delivery device selected in a group comprising a transmucosal device and a vaginal ring.

In some embodiments of the said vaginal composition, the said estrogen is estradiol or a derivative thereof.

In some embodiments of the said vaginal composition, the said vitamin D analog is selected in a group comprising calcitriol and calcipotriol.

This invention also concerns a composition comprising a combination of estrogen and vitamin D or vitamin D analog at a daily dosage delivery of (i) estrogen ranging from 1 µg to 100 µg estrogen of estradiol equivalent and (ii) vitamin D or analog ranging from 7.5 µg to 100 µg of vitamin D equivalent for its use as a vaginal pharmaceutical composition.

In some preferred embodiments of the use described above, the daily dosage delivery of estrogen ranges from 1 µg to 70 µg.

In some preferred embodiments of the use described above, the daily dosage delivery of estrogen ranges from 1 µg to 10 µg.

In some embodiments of the use described above, the said composition comprises a combination of estradiol and calcitriol at a daily dosage delivery of (i) estradiol ranging from 1 µg to 10 µg and (ii) calcitriol ranging from 0.25 µg to 1 µg.

This invention also pertains to a composition comprising a combination of estrogen and vitamin D or vitamin D analog at a daily dosage delivery of (i) estrogen ranging from 1 µg to 100 µg estrogen of estradiol equivalent and (ii) vitamin D or analog ranging from 7.5 µg to 100 µg of vitamin D equivalent for its use for preventing or treating vaginal atrophy.

In some preferred embodiments of the use described above, the daily dosage delivery of estrogen ranges from 1 µg to 70 µg.

In some preferred embodiments of the use described above, the daily dosage delivery of estrogen ranges from 1 µg to 10 µg.

In some embodiments of the use described above, the said composition comprises a combination of estradiol and calcitriol at a daily dosage delivery of (i) estradiol ranging from 1 µg to 10 µg and (ii) calcitriol ranging from 0.25 µg to 1 µg.

This invention also relates to a method for preventing or treating vaginal atrophy comprising a step of administering the vaginal composition described throughout the present specification to a woman in need thereof.

DESCRIPTION OF THE FIGURES

FIG. 1 depicts the evolution of body weight post-ovariectomy and during the 6-week treatment period. Ordinate: Body weight, as expressed in grams. Abscissa: time period following ovariectomy, as expressed in days. Data are represented as mean values +/− SEM, using the two-way ANOVA test. Although the curves corresponding to the various experimental conditions may be difficult to identify in the black and white FIG. 1, the results of FIG. 1 show that there is no statistically significant differences in the body weight between the different experimental conditions.

In FIG. 2, significant results denoted "**" were calculated for the following conditions: Estradiol 0.4 µg: Estradiol 0.2 µg+Calcitriol 0.1 µg; Estradiol 0.2 µg+Calcitriol 0.08 µg; Estradiol 0.4 µg+Calcitriol 0.006 µg: Estradiol 0.02 µg+Calcitriol 0.006 µg; and Estradiol 0.02 µg+0.075 µg.

DETAILED DESCRIPTION OF THE INVENTION

Figure 1:
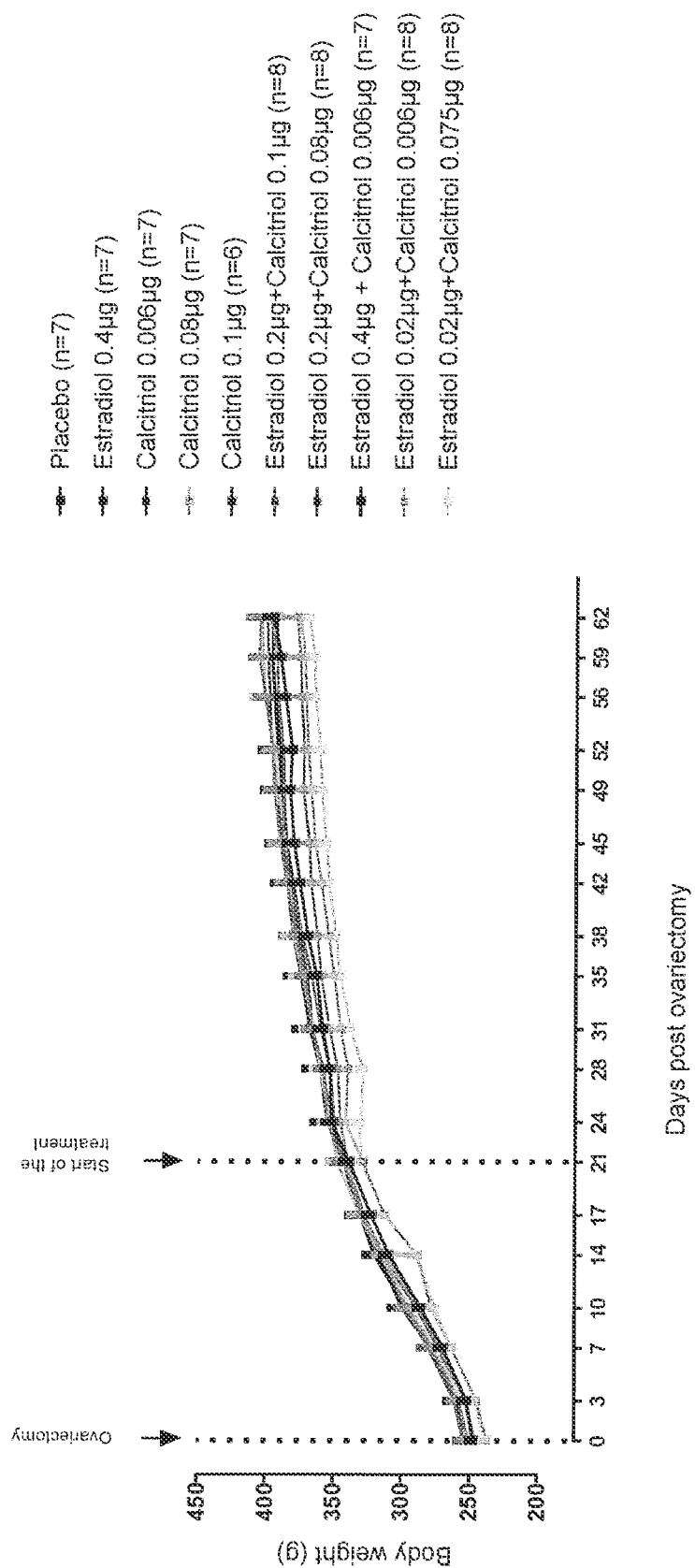
FIG. 1 illustrates a graph of body weight evolution.

Any citation mentioned herein is incorporated by reference.

This invention relates to an estrogen-based composition for preventing or treating vaginal atrophy, and especially post-menopausal vaginal atrophy.

The present inventors have performed an extensive research with the aim of conceiving a pharmaceutical composition for preventing or treating vaginal atrophy with the aim of obtaining a composition that shall be as effective as the known compositions in its preventive or curative effect, and that shall be safer than the known compositions.

As described in detail in the present specification, the inventors have conceived a specific pharmaceutical composition which is endowed with a local action of the selected estrogen on the vaginal mucosa and which is believed to possess a limited or even no estrogen systemic action, and which is thus safer than the known pharmaceutical compositions.

The present inventors have conceived an estrogen-based pharmaceutical composition comprising vitamin D or a vitamin D analog, which pharmaceutical composition is under a physical form which is suitable for a local release of the active ingredients to the vaginal mucosa.

According to a first aspect, a pharmaceutical composition according to the invention releases locally an estrogen active ingredient at a daily amount which is lower than the daily amount which is described in the an as an effective dose for preventing or treating vaginal atrophy, especially vaginal atrophy in post-menopausal women.

As it is shown in the examples herein, a pharmaceutical composition according to the invention, when administered locally to individuals affected with vaginal atrophy, allows reversing vaginal atrophy by increasing the thickness of the vaginal epithelium and especially by increasing the maturation status of the vaginal epithelium, as illustrated notably by the high increase of the cornified cells content contained therein.

According to a further aspect, a pharmaceutical composition according to the invention releases locally vitamin D or vitamin D analog active ingredient at a daily amount which is at most the highest amount which is recommended by the health agencies, which includes the Food and Drug Administration in the US and the European Food Safety Authority (EFSA Journal 2012; 10(7):2813).

According to a still further aspect, a pharmaceutical composition according to the invention is at least as effective for preventing or treating vaginal atrophy as known estrogen-based compositions although the said pharmaceutical composition comprises a very low amount of the said estrogen active ingredient.

According to a yet further aspect, a pharmaceutical composition according to the invention, because it contains a very low amount of an estrogen active ingredient, is believed to be endowed with a decreased risk of side effects, and especially with a decreased risk of hyperplasia or carcinoma, in comparison with the known compositions for treating vaginal atrophy, including the known compositions for locally treating vaginal atrophy. Indeed, because a vaginal composition according to the invention comprises a very low amount of estrogen, then a risk of side effects caused by systemic passage of estrogen is far lower than with the low dose estrogen compositions known in the art.

According to still a further aspect, a pharmaceutical composition according to the invention, because it contains at most the highest amount of vitamin D or vitamin D analog active ingredient recommended by the health agencies, is believed to be endowed with a decreased risk of side effects, and especially with a decreased risk of hypercalcemia.

The present invention relates to a vaginal composition comprising a combination of estrogen and vitamin D or a vitamin D analog at a daily dosage delivery of (i) estrogen ranging from 1 μg to 100 μg estrogen of estradiol equivalent and (ii) vitamin D or analog ranging from 7.5 μg to 100 μg of vitamin D equivalent.

In some preferred embodiments, the daily dosage delivery of estrogen ranges from 1 μg to 70 μg.

In some other preferred embodiments, the daily dosage delivery of estrogen ranges from 1 μg to 10 μg.

In some embodiments, the said vaginal composition comprises a combination of estradiol and calcitriol at a daily dosage delivery of (i) estradiol ranging from 1 μg to 10 μg and (ii) calcitriol ranging from 0.25 μg to 1 μg.

In some embodiments, the vaginal composition comprises a combination of estrogen and vitamin D or a vitamin D analog at a daily dosage delivery of (i) estrogen ranging from 2 μg to 10 μg estrogen of estradiol equivalent and (ii) vitamin D or analog ranging from 7.5 μg to 100 μg of vitamin D equivalent.

As used herein, the expression "estrogen of estradiol equivalent" means an amount of a selected estrogen which is expressed as the equivalent amount of estradiol. Estrogen equivalency is described elsewhere in the present specification.

As used herein, the expression "of vitamin D equivalent" means an amount of a selected vitamin D analog which is expressed as the equivalent amount of vitamin D. Vitamin D equivalency is described elsewhere in the present specification.

As used herein, the expression "daily dosage delivery" may be used interchangeably with the expression "daily delivery amount". These expressions mean the amount of the considered active ingredient (i.e. estrogen and vitamin D or vitamin D analog, respectively) which is released by the vaginal composition according to the invention. In most embodiments, the amount of an active ingredient released by a vaginal composition according to the invention is also the amount of the said active ingredient which is comprised in the said composition.

In embodiments of a vaginal composition according to the invention which are conceived for a daily administration of the said composition, the "daily dosage delivery" or "daily delivery amount" of a given active ingredient comprised therein (i.e. estrogen and vitamin D or vitamin D analog, respectively) is the amount of the said active ingredient comprised in the dosage unit which is to be administered.

In other embodiments of a vaginal composition according to the invention which are conceived for releasing the active ingredients for a period of time of two days or more, then the "daily dosage delivery" or "daily delivery amount" of a given active ingredient comprised therein (i.e. estrogen and vitamin D or vitamin D analog, respectively) is the amount of the said active ingredient, comprised in the dosage unit, which is released daily by the said vaginal composition. The one skilled in the art readily understands that a vaginal composition aimed at releasing a given daily amount of an active ingredient during a period of time of, e.g., seven days, shall comprise an amount of the said active ingredient which is at least seven times the said given daily amount.

The expression "of estradiol equivalent" means that the specified amount of estrogen is expressed as the amount in estradiol equivalent value, the said equivalency being described elsewhere in the present specification.

The expression "of vitamin D equivalent" means that the specified amount of vitamin D or analog is expressed as the amount in vitamin D equivalent value, the said equivalency being described elsewhere in the present specification.

A daily dosage of vitamin D ranging from 7.5 μg to 100 μg consists of a daily dosage ranging from 300 IU to 4000 IU of vitamin D, as it is well known in the art.

In some embodiments of the vaginal composition wherein vitamin D or analog is calcitriol or calcipotriol, then the said vaginal composition comprises calcitriol or calcipotriol at a daily dosage delivery ranging from 0.075 μg to 1.000 μg, which corresponds to 7.5 μg to 100 μg of vitamin D equivalent.

A daily dosage of calcitriol or calcipotriol ranging from 0.075 μg to 1.00 μg encompasses a daily dosage of calcitriol or calcipotriol ranging from 0.25 μg to 1.00 μg, and a daily dosage of calcitriol or calcipotriol ranging from 0.5 μg to 1.00 μg.

In preferred embodiments, the combination of estrogen and vitamin D or vitamin D analog is the sole combination of active ingredients inducing an effect on vaginal atrophy that is comprised in a vaginal composition according to the invention.

Illustratively, a vaginal composition does not comprise any selective estrogen receptor modulator compound (also termed "SERM"), such as raloxifene, tamoxifen, clomifene, ormeloxifene, toremifene, lasofoxifene or ospermifene.

In most preferred embodiments, estrogen and vitamin D or vitamin D analog are the sole active ingredients comprised in a vaginal composition according to the invention.

A vaginal composition according to the invention may comprise one or more estrogens.

A vaginal composition comprising estrogen at a daily dosage ranging from 2 μg to 10 μg of estradiol equivalent comprises estrogen at a daily dosage amount ranging from 0.029 μg/kg to 0.142 μg/kg of estradiol equivalent, based on a woman weighing 70 kg.

In some embodiments, the vaginal composition comprises estrogen at a daily dosage ranging from 1 μg to 10 μg of estradiol equivalent comprises estrogen at a daily dosage amount ranging from 0.014 μg/kg to 0.142 μg/kg of estradiol equivalent, based on a woman weighing 70 kg.

In some embodiments, the vaginal composition comprises estrogen at a daily dosage ranging from 1 μg to 100 μg of estradiol equivalent comprises estrogen at a daily dosage amount ranging front 0.014 μg/kg to 1.42 μg/kg of estradiol equivalent, based on a woman weighing 70 kg.

In most preferred embodiments, a vaginal composition according to the invention comprises only one estrogen.

In some embodiments, a vaginal composition according to the invention comprises an amount of estrogen for a daily dosage delivery of an amount of estradiol equivalent ranging from 2 μg to 7.5 μg. According to these embodiments, a vaginal composition according to the invention comprises an amount of estradiol equivalent ranging from 0.029 μg/kg to 0.11 μg/kg, based on a woman weighing 70 kg.

In some embodiments, a vaginal composition according to the invention comprises an amount of estrogen for a daily dosage delivery of an amount of estradiol equivalent ranging from 1 μg to 7.5 μg. According to these embodiments, a vaginal composition according to the invention comprises an amount of estradiol equivalent ranging from 0.014 μg/kg to 0.11 μg/kg, based on a woman weighing 70 kg.

In some embodiments, a vaginal composition according to the invention comprises vitamin D or an analog thereof at a daily dosage delivery of vitamin D or analog ranging from 7.5 μg to 100 μg of vitamin D equivalent.

In some preferred embodiments, vitamin D analog is calcitriol. In these embodiments, a vaginal composition according to the invention comprises calcitriol at a daily dosage delivery* ranging from 0.075 μg to 1.000 μg of calcitriol. In some aspects of these preferred embodiments, a vaginal composition according to the invention comprises calcitriol at a daily dosage delivery ranging from 0.25 µg to 1.00 µg of calcitriol. In some other aspects of these preferred embodiments, a vaginal composition according to the invention comprises calcitriol at a daily dosage ranging from 0.50 µg to 1.00 µg of calcitriol.

Thus, in some preferred embodiments, a vaginal composition as described herein comprises a combination of estradiol and calcitriol at a daily dosage delivery of (i) estradiol ranging from 1 µg to 10 µg and (ii) calcitriol ranging from 0.25 µg to 1 µg.

As used herein, a vaginal composition encompasses a pharmaceutical composition for local administration of the active ingredients in view of the release of these active ingredients at the expected amount at the vaginal mucosa.

In some embodiments of the vaginal composition according to the invention, the said composition is under a pharmaceutical form comprising the daily dosage amount of the combined estrogen and vitamin D or analog active ingredients.

In some other embodiments of the vaginal composition according to the invention, the said composition is under a pharmaceutical form comprising an amount of the combined estrogen and vitamin D or analog that represents a plurality of daily dosage amounts, the said pharmaceutical form releasing each day the required daily amount of the said combined active ingredients.

In all embodiments, a vaginal composition according to the invention comprises an amount of estrogen allowing the release of a daily amount of estrogen ranging from 1 µg to 100 µg estrogen of estradiol equivalent, which encompasses of a daily amount of estrogen ranging from 1 µg to 7.5 µg estrogen of estradiol equivalent.

In some embodiments, the daily dosage delivery of estrogen ranges from 1 µg to 70 µg.

In some other embodiments, the daily dosage delivery of estrogen ranges from 1 µg to 10 µg.

In some embodiments, a vaginal composition according to the invention comprises an amount of estrogen allowing the release of a daily amount of estrogen ranging from 2 µg to 10 µg estrogen of estradiol equivalent, which encompasses of a daily amount of estrogen ranging from 2 µg to 7.5 µg estrogen of estradiol equivalent.

In all embodiments, a vaginal composition according to the invention comprises an amount of vitamin D or analog allowing the release of a daily amount of the said vitamin D or analog ranging from 7.5 µg to 100 µg of vitamin D equivalent.

In some embodiments, a vaginal composition according to the invention comprises an amount of vitamin D or analog allowing the release of a daily amount of the said vitamin D or analog ranging from 7.5 µg to 100 µg of vitamin D equivalent. In some embodiments, a vaginal composition according to the invention comprises an amount of vitamin D or analog allowing the release of a daily amount of the said vitamin D or analog ranging from 7.5 µg to 25 µg of vitamin D equivalent In some embodiments, a vaginal composition according to the invention comprises an amount of vitamin D or analog allowing the release of a daily amount of the said vitamin D or analog ranging from 15 µg to 100 µg of vitamin D equivalent. In some embodiments, a vaginal composition according to the invention comprises an amount of vitamin D or analog allowing the release of a daily amount of the said vitamin D or analog ranging from 15 µg to 25 µg of vitamin D equivalent In some embodiments, a vaginal composition according to the invention comprises (i) an amount of estradiol allowing the release of a daily amount of estradiol ranging from 1 µg to 10 µg. and (ii) an amount of calcitriol allowing the release of a daily amount of calcitriol ranging from 0.25 µg and 1.000 µg.

In all embodiments of a vaginal composition according to the invention, the combination of estrogen and vitamin D or vitamin D analog is further combined with one or more physiologically acceptable excipients.

In all embodiments of a vaginal composition according to the invention, the one or more physiological excipients are present in a quantity sufficient so as to amount at 100% of the weight of the vaginal composition, or alternatively at 100% of the volume of the vaginal composition, depending on the amount unit which is used.

In embodiments of a vaginal composition according to the invention wherein the said composition is under a pharmaceutical form suitable for a daily administration, such as a pharmaceutical form selected in a group comprising a cream, a gel, a suppository (such as an ovule, a capsule or a tablet), then a daily unit dosage of the said vaginal composition comprises (i) an estrogen at an amount ranging from 1 µg to 100 µg of estradiol equivalent and (ii) vitamin D or analog ranging from 7.5 µg to 100 µg of vitamin D equivalent. In some aspects of these embodiments, a daily unit dosage of the said vaginal composition comprises (i) an estrogen at an amount ranging from 1 µg to 100 µg of estradiol equivalent and (ii) vitamin D or analog ranging from 15 µg to 100 µg of vitamin D equivalent. In some aspects of these embodiments, a daily unit dosage of the said vaginal composition comprises (i) an estrogen at an amount ranging from 1 µg to 100 µg of estradiol equivalent and (ii) vitamin D or analog ranging from 15 µg to 25 µg of vitamin D equivalent. In some aspects of these embodiments, a daily unit dosage of the said vaginal composition comprises (i) an estrogen at an amount ranging from 1 µg to 10 µg of estradiol equivalent and (ii) vitamin D or analog ranging from 7.5 µg to 100 µg of vitamin D equivalent. In some aspects of these embodiments, a daily unit dosage of the said vaginal composition comprises (i) an estrogen at an amount ranging from 1 µg to 7.5 µg of estradiol equivalent and (ii) vitamin D or analog ranging from 7.5 µg to 100 µg of vitamin D equivalent. In some further aspects of these embodiments, a daily unit dosage of the said vaginal composition comprises (i) an estrogen at an amount ranging from 1 µg to 10 µg of estradiol equivalent and (ii) vitamin D or analog ranging from 15 µg to 100 µg of vitamin D equivalent. In still some further aspects of these embodiments, a daily unit dosage of the said vaginal composition comprises (i) an estrogen at an amount ranging from 1 µg to 7.5 µg of estradiol equivalent and (ii) vitamin D or analog ranging from 15 µg to 100 µg of vitamin D equivalent. In yet some further aspects of these embodiments, a daily unit dosage of the said vaginal composition comprises (i) an estrogen at an amount ranging from 1 µg to 10 µg of estradiol equivalent and (ii) vitamin D or analog ranging from 15 µg to 25 µg of vitamin D equivalent. In still some further aspects of these embodiments, a daily unit dosage of the said vaginal composition comprises (i) an estrogen at an amount ranging from 1 µg to 7.5 µg of estradiol equivalent and (ii) vitamin D or analog ranging from 15 µg to 25 µg of vitamin D equivalent.

In some of these embodiments, a vaginal composition according to the invention a daily unit dosage of the said vaginal composition comprises (i) estradiol at an amount ranging from 1 µg to 10 µg and (ii) calitriol or calcipotriol at an amount ranging from 0.075 µg to 1.000 µg. In some aspects of these embodiments, a daily unit dosage of the said vaginal composition comprises (i) an estradiol at an amount ranging from 1 µg to 7.5 µg and (ii) calitriol or calcipotriol ranging from 0.075 µg to 1.00 µg. In some further aspects of these embodiments, a daily unit dosage of the said vaginal composition comprises (i) an estradiol at an amount ranging from 1 µg to 10 µg and (ii) calcitriol or calcipotriol ranging from 0.5 µg to 1.00 µg. In still some further aspects of these embodiments, a daily unit dosage of the said vaginal composition comprises (i) an estradiol at an amount ranging from 1 µg to 7.5 µg and (ii) calitriol or calcipotriol ranging from 0.5 µg to 4.00 µg. In yet some further aspects of these embodiments, a daily unit dosage of the said vaginal composition comprises (i) an estradiol at an amount ranging from 1 µg to 10 µg of and (ii) calitriol or calcipotriol ranging from 0.25 µg to 1.00 µg. In still some further aspects of these embodiments, a daily unit dosage of the said vaginal composition comprises (i) an estradiol at an amount ranging from 1 µg to 7.5 µg and (ii) calitriol or calcipotriol ranging from 0.25 µg to 1.00 µg. In yet some further aspects of these embodiments, a daily unit dosage of the said vaginal composition comprises (i) an estradiol at an amount ranging from 1 µg to 10 µg of and (ii) calitriol or calcipotriol ranging from 0.5 µg to 1.00 µg. In still some further aspects of these embodiments, a daily unit dosage of the said vaginal composition comprises (i) an estradiol at an amount ranging from 1 µg to 7.5 µg and (ii) calitriol or calcipotriol ranging from 0.5 µg to 1.00 µg.

In some of these embodiments, a vaginal composition according to the invention a daily unit dosage of the said vaginal composition comprises (i) estradiol at an amount ranging from 1 µg to 10 µg and (ii) calitriol at an amount ranging from 0.25 µg to 1.000 µg.

In embodiments of the vaginal composition according to the invention wherein the said composition is under a pharmaceutical form suitable for a continuous release of the combined active ingredients during a plurality of days, such as about 15 days or about 30 days, such as comprised in a transmucosal delivery system or in a vaginal ring, then the said vaginal composition comprises an amount of the combined active ingredients which is at minimum a multiple of the required daily dosage that is released by the said delivery system or by the said vaginal ring.

For example, in embodiments wherein the vaginal composition is comprised in a delivery system, such as a transmucosal delivery system or a vaginal ring, that shall remain in the vaginal cavity for a period of time of 15 days, then the said vaginal composition may comprise at minimum a combination of estrogen and vitamin D or a vitamin D analog at a daily dosage delivery of (i) estrogen ranging from 15 µg to 1500 µg estrogen of estradiol equivalent and (ii) vitamin D or analog ranging from 112.5 µg to 1500 µg of vitamin D equivalent.

For example, in some other embodiments wherein the vaginal composition is comprised in a delivery system, such as a transmucosal delivery system or a vaginal ring, that shall remain in the vaginal cavity for a period of time of 15 days, then the said vaginal composition may comprise at minimum a combination of estrogen and vitamin D or a vitamin D analog at a daily dosage delivery of (i) estrogen ranging from 30 µg to 150 µg estrogen of estradiol equivalent and (ii) vitamin D or analog ranging from 112.5 µg to 1500 µg of vitamin D equivalent.

In such embodiments, the amount of each of the combined active ingredients is preferably higher than the sole amount required for the time period wherein the delivery system is located in the vaginal cavity, so as to ensure that the required daily amount of the combined active ingredients will be actually released and will remain as constant as possible during the whole said time period.

Estrogen

As used herein, "estrogen" encompasses estrogenic steroids selected in a group comprising estradiol (17-β-estradiol), estradiol valerate, estradiol benzoate, estradiol 17β-cypionate, estradiol dipropionate, estradiol enanthate, estropipate, equilenin, equilin, estriol, estriol succinate, estrone, ethinyl estradiol, estetrol, quinestrol, quinestranol, conjugated estrogens (equine or synthetic), esterified estrogens, and mixtures thereof.

The estrogen may be selected, for example, from a group comprising of ethinyl estradiol, 17-[beta]-estradiol, conjugated estrogens, mestranol, estetrol, estrone and esters, prodrugs and salts thereof. An exemplary ester is estradiol acetate. Preferred salts of estrone include, but are not limited to the sodium, sulfate and piperate salt.

For the conjugated estrogens, 1.25 mg conjugated estrogens is equivalent to a daily dose of 15 µg ethinyl estradiol. The most preferred estrogen is estradiol.

Determination of estradiol equivalent potency is well understood and readily accomplished by those of ordinary skill in the art. Illustratively, for determining the estradiol equivalent value of an estrogen amount, the one skilled in the art may refer to the European patent application no EP 0253607 or to the PCT application no. WO 2007/089733. Still illustratively, 30 µg of ethinyl estradiol is roughly equivalent to 60 µg of mestranol or 2 mg of 17 beta estradiol.

In preferred embodiments of a vaginal composition according to the invention, the estrogen is estradiol The term "estradiol" refers to (17beta)-estra-1,3,5(10)-triene-3,17-diol. Estradiol is also interchangeably called 17beta-estradiol, oestradiol, or E2.

In some embodiments, the estradiol starting product for manufacturing a vaginal composition according to the invention may be provided in an anhydrous or hemi-hydrate form. Indeed, the anhydrous form or the hemihydrate form can be substituted for the other by accounting for the water or lack of water according to well-known and understood techniques The term "solubilized estradiol" means that the estradiol or a portion thereof is solubilized or dissolved in one or more solubilizing agent(s) for preparing a vaginal composition disclosed herein. Solubilized estradiol may include estradiol that is about 80% solubilized, about 85% solubilized, about 90% solubilized, about 95% solubilized, about 96% solubilized, about 97% solubilized, about 98% solubilized, about 99% solubilized or about 100% solubilized. In some embodiments, the estradiol is "fully solubilized" with all or substantially all of the estradiol being solubilized or dissolved in the solubilizing agent. Fully solubilized estradiol may include estradiol that is about 97% solubilized, about 98% solubilized, about 99% solubilized or about 100% solubilized. Solubility can be expressed as a mass fraction (% w/w, which is also referred to as wt %).

In some embodiments, estradiol is used in a micronized form. The term "micronized estradiol," as used herein, include micronized micronized estradiol having an $X_{50}$ particle size value below about 15 microns or having an $X_{90}$ particle size value below about 25 microns. The term "$X_{50}$" means that one-half of the particles in a sample are smaller in diameter than a given number. For example, micronized estradiol having an $X_{50}$ of 5 microns means that, for a given sample of micronized estradiol, one-half of the particles have a diameter of less than 5 microns. Similarly, the term "$X_{90}$" means that ninety percent (90%) of the particles in a sample are smaller in diameter than a given number.

Vitamin D and Vitamin D Analogs

As intended herein a "vitamin D analog" is a compound that binds to the vitamin D receptor (VDR).

Tests for determining the ability of a vitamin D analog or of a vitamin D receptor modulator to bind to the vitamin D receptor are well known to the person skilled in the art. Preferably, this ability may be evaluated by measuring the specific binding of the said analog or of the vitamin D receptor modulator on a cell extract. For example, in a typical binding experiment, soluble cell extract obtained by sonication is incubated with increasing concentration of vitamin D analog or of vitamin D receptor modulator. Bounds and free analogs can be separated by the hydroxylapatite method. Specific binding may be calculated by subtracting non-specific binding obtained in the presence of an excess 1,25-(OH)2D3 from the total binding measured in absence of 1,25-(OH)2D3 (Skowronski et al. (1995) Endocrynology 136(1):20-26).

As used herein, active form of vitamin D is known as 1α,25-dihydroxyvitamin D3 (1,25(OH)$_2$D3 or calcitriol).

As used herein, vitamin D analogs encompass cholecalciferol (also termed as vitamin D3) and ergocalciferol (also termed as vitamin D2) and their metabolites as well as synthetic cholecalciferol and ergocalciferol analogs. These synthetic cholecalciferol and ergocalciferol analogs comprise such categories of compounds as the 5,6 trans-cholecalciferols and 5,6 trans-ergocalciferols, the fluorinated cholecalciferols, the side chain homologated cholecalciferols and side chain homologated 22 cholecalciferols the side chain truncated cholecalciferols, the 19-nor cholecalciferols and ergocalciferols and the 10,19-dihydrovitamin D compounds. Some specific examples include but are not limited to cholecalciferol (vitamin D3, calciol), ergocalciferol (vitamin D2, ercalciol), alphacalcidol (1 alpha-hydroxy vitamin D3), calcidiol (25-hydroxyvitamin D3), calcitriol (1,25-dihyroxyvitamin D3), calcifediol, calcipotriol (calcipotriene), 22-oxacalcitriol (OCT), paricalcitol (19-Nor-1 alpha, 25-dihydroxyvitamin D2), doxercalciferol, eldecalcitol, dihydrotachysterol-2 (DHT-2).

The vitamin D analog 22-oxacalcitriol (OCT) differs from 1,25(OH)$_2$D3 by virtue of an oxygen atom replacing carbon-22 on the side chain.

Paricalcitol is a vitamin D2 derived sterol lacking the carbon-19 methylene group found in all natural vitamin D metabolites.

Doxercalciferol (1α-hydroxyvitamin D2), like alfacalcidol (1α-hydroxyvitamin D3), is a pro-drug which is hydroxylated in the liver to 1α,25(OH)2D2.

Dihydrotachysterol-2 (DHT-2), hydroxylated in vivo to 25(OH)DHT2 is also of interest for a vaginal composition according to the invention.

Vitamin D and vitamin D analogs are well known by the one skilled in the art, as well as their respective methods of synthesis. Further, vitamin D and analogs thereof are commercially available to the one skilled in the art.

Pharmaceutical Forms

Vaginal compositions according to the invention may be provided in various pharmaceutical forms that are suitable tor the local delivery of the combined estrogen and vitamin D or vitamin D analog to the vaginal mucosa.

Different pharmaceutical forms for administering drugs intravaginally have been described, such as suppositories (such as ovules, capsules and tablets), solutions, creams, foams, gels, films and vaginal rings. Intravaginal delivery systems are described in patents and patent applications such as U.S. Pat. No. 6,086,908, no US 2005/0276836, U.S. Pat. No. 6,086,909, no EP 0889724, U.S. Pat. No. 7,004,171, no US 2008/193428 and U.S. Pat. No. 5,989,581, wherein intravaginal release systems are described and between the alternatives vaginal rings are mentioned.

A vaginal composition according to the invention may be also provided in syringe-like applicators for local vaginal administration.

Vaginal cream compositions are for example described in the patent applications and patents no. EP 2849735, WO 2006/023496 and U.S. Pat. No. 5,514,698. Vaginal tablet compositions are for example described in the patent applications and patents no. WO 2015/135915, US 2011/159091, U.S. Pat. No. 3,062,715 and EP 0900564.

Vaginal film compositions are for example described in the patent applications no WO 2004/103232 and US 2005/070501.

A vaginal composition according to the invention may be provided as a vaginal cream or gel, a vaginal suppository (such as a vaginal ovule, a vaginal capsule, a vaginal tablet), or may be comprised in a vaginal delivery system such as a transmucosal device, a sponge-like device or a vaginal ring.

As used herein, a "vaginal suppository" encompasses a vaginal ovule, a vaginal tablet or a vaginal capsule.

Vaginal suppositories are known in the art, and may be made of glycerin, fatty acids, and similar type substances that dissolve at body temperature. As the suppository dissolves, the combined estrogen and vitamin D or vitamin D analog will be released.

In some embodiments, a vaginal suppository according to the invention comprises an inert vehicle. As used herein the term "inert vehicle" refers to a vehicle which brings the active substance, in this case lactic acid or a salt thereof in contact with the vaginal tissue. The inert vehicle enables the fabrication of a suppository which is relatively solid at room temperature and in a dry environment, but which melts at body temperature and in contact with body fluids. Any inert vehicle which has the above characteristics may be used, but typically polyethylene glycol (PEG) is used. In embodiments of the invention, the inert vehicle comprises polyethylene glycol 600 and polyethylene glycol 4000. The ratio between PEG 600 and PEG 4000 may be varied which allows for the dissolution time of the vaginal suppositories to be varied. The properties of the inert vehicle determines the dissolution time of the vaginal suppositories in the vagina.

In some embodiments, a vaginal composition according to the invention is under the form of an ovule, e.g. a pharmaceutical form wherein the said combined estrogen and vitamin D or vitamin D analog are comprised within a lipophilic suppository base. Illustratively, the one skilled in the art may prepare a vaginal composition according to the invention starting from a lipophilic suppository base such as the starting suppository composition marketed under the name Ovucire® by the French company Gatefossé.

An ovule of the present invention may be prepared according to a method comprising the steps of:
  a) melting the Ovucire® mixture at a temperature of 45-80° C.;
  b) precooling the mixture by slowly stirring until a mass temperature of 40-60° C. is reached and then adding a volume of 50 µl of placebo or the active ingredient(s) liquid material under vigorous stirring;
d) keeping stirring slowly until the mold temperature reaches 35-50° C.;
e) filling the molds with the mass;
f) cooling the ovules in the molds; and
g) sealing the molds.

A vaginal composition according to the invention may be provided under the form of a vaginal cream or a vaginal gel. A "gel" is a colloid in which a disperse phase combines with a dispersion medium to produce a jelly-like, solid or semi-solid material. Although a variety of compounds may be employed, water is usually employed as the dispersion medium for the gel to optimize biocompatibility. Other possible dispersion mediums include non-aqueous solvents, including glycols, such as propylene glycol, butylene glycol, triethylene glycol, hexylene glycol, polyethylene glycols, ethoxydiglycol, and dipropyleneglycol; alcohols, such as ethanol, n-propanol, and isopropanol; triglycerides; ethyl acetate; acetone; triacetin; and combinations thereof. Typically, the dispersion medium (e.g., water) constitutes greater than about 75 wt/vol %, in some embodiments greater than about 90 wt/vol %, and in some embodiments, from about 95 wt/vol % to about 99 wt/vol % of the vaginal treatment composition. As used herein, the designation "wt/vol %" or "wt/vol" or refers to the value obtained by dividing the weight of a substance (in grams) by the volume of the solution (in milliliters), and then multiplying by 100.

A vaginal composition according to the invention may be comprised in specific delivery systems such as transmucosal delivery systems or also in vaginal ring delivery systems.

As used herein, the term "transmucosal" refers to delivery, administration or application of a drug by means of direct contact with skin or mucosa. Such delivery, administration or application is also known us transmucosal. As used herein, "mucosal" includes mucosa, which includes vaginal mucosa.

As used herein, "transmucosal drug delivery system" refers to a system (e.g., a device) comprising a composition that releases the combination of estrogen and vitamin D or vitamin D analog upon application to the vaginal mucosa. A transmucosal drug delivery system may comprise a backing layer, a drug-containing layer, and a release liner layer. In some embodiments, the transdermal drug delivery system is a substantially non-aqueous, solid form, capable of conforming to the surface with which it comes into contact, and capable of maintaining such contact so as to facilitate topical application on the vaginal mucosa without adverse physiological response, and without being appreciably decomposed by aqueous contact during topical application to a subject. Many such systems are known in the art and commercially available, such as transmucosal drug delivery patches. As described below, in one embodiment, the transmucosal drug delivery system comprises a drug-containing polymer matrix that comprises a pressure-sensitive adhesive or bioadhesive, and is adopted tor direct application to a user's (e.g., a subject's) skin. In other embodiments, the polymer matrix is non-adhesive and may be provided with separate adhesion means (such as a separate adhesive layer) for application and adherence to the user's vaginal mucosa. Transmucosal delivery systems are notably described in the patent applications and patents such as CN 102641548, WO 2005/016321, WO 2004/067063, U.S. Pat. No. 5,204,108. US 2004/043071 and JP 3 705 620.

As used herein, "polymer matrix" refers to a polymer composition which contains one or more drugs. In some embodiments, the matrix comprises a pressure-sensitive adhesive polymer or a bioadhesive polymer. In other embodiments, the matrix does not comprise a pressure-sensitive adhesive or bioadhesive. As used herein, a polymer is an "adhesive" if it has the properties of an adhesive per se, or if it functions as an adhesive by the addition of tackifiers, plasticizers, crosslinking agents or other additives. Thus, in some embodiments, the polymer matrix comprises a pressure-sensitive adhesive polymer or a bioadhesive polymer, with estrogen dissolved or dispersed therein. The polymer matrix also may comprise tackifiers, plasticizers, crosslinking agents or other additives.

A vaginal composition according to the invention may also be comprised in a vaginal ring.

Many of vaginal ring devices known by the one skilled in the an may be used for the purpose of the present invention.

In some embodiments, a vaginal ring delivery system for use with a vaginal composition according to the invention may be manufactured as it follows. A homogeneous blend of all the ingredients to be injected into the ring molds was prepared. First the required amounts of each ingredient were weighed: Polymer A, release modifier agent, if applicable, and meloxicam. These ingredients were mixed until homogenization and the polymer B was added under constant mixing. The mixture was injected into ring molds at room temperature and then kept in an oven at 105° C. for 1 hour. Subsequently molds were cooled and the formed rings were disassembled from their respective molds obtaining the final product.

Vaginal rings and methods for preparing the same are notably described in the patent applications and patents WO 2016/054002, EP 2 799042, US 2015/328319. WO 2011/011099, WO2013/098591 and US 2013/269706.

Methods of Prevention and Treatment of Vaginal Atrophy

The present invention further relates to a method for preventing or treating vaginal atrophy, which method comprises a step of administering a vaginal composition as described in the present specification to a woman in need thereof.

Thus, this invention to a method for preventing or treating vaginal atrophy comprising a step of administering, to a woman in need thereof, a vaginal composition comprising a combination of estrogen and vitamin D or a vitamin D analog at a daily dosage delivery of (i) estrogen ranging from 1 µg to 100 µg estrogen of estradiol equivalent and (ii) vitamin D or analog ranging from 7.5 µg to 100 µg of vitamin D equivalent.

In some embodiments, the daily dosage delivery of estrogen ranges from 1 µg to 70 µg.

In some other embodiments, the daily dosage delivery of estrogen ranges from 1 µg to 10 µg.

In some other embodiments of the method, the said vaginal composition comprises estradiol and calcitriol at a daily dosage delivery of (i) estradiol ranging from 1 µg to 10 µg and (ii) calitriol ranging from 0.25 µg to 1.000 µg.

In some other embodiments, the invention also relates to a method for preventing or treating vaginal atrophy comprising a step of administering, to a woman in need thereof, a vaginal composition comprising a combination of estrogen and vitamin D or a vitamin D analog at a daily dosage delivery of (i) estrogen ranging from 2 µg to 10 µg estrogen of estradiol equivalent and (ii) vitamin D or analog ranging from 7.5 µg to 100 µg of vitamin D equivalent.

In some embodiments of the said composition, the said estrogen is estradiol.

In some embodiments of the said composition, the said vitamin D or vitamin D analog is selected in a group comprising calcitriol and calcipotriol.

In some embodiments of the method, the said vaginal composition is liquid, solid or semi-solid.

In some embodiments, the said vaginal composition is a cream or a gel composition.

In some embodiments, the said vaginal composition is presented as daily unit dosage form selected in a group comprising a capsule, an ovule, a tablet and a suppository.

In some embodiments, the said vaginal composition is comprised in a delivery device selected in a group comprising a transmucosal device and a vaginal ring.

In the embodiments of the method wherein the vaginal composition is under the form of a cream, a gel or a suppository (such as a capsule, an ovule or a tablet), the said composition is preferably administered at least once daily, which includes one daily administration of the vaginal composition.

In the embodiments of the method wherein the vaginal composition is comprised in a transmucosal delivery system or a vaginal ring, the said transmucosal delivery system or the said vaginal ring is placed in the vaginal cavity at defined periodicity and the vaginal composition is continuously released from the transmucosal delivery system or vaginal ring at a rate which is appropriate for releasing the combined estrogen and vitamin D or vitamin D analog at a daily dosage delivery of (i) estrogen ranging from 1 µg to 10 µg estrogen of estradiol equivalent and (ii) vitamin D or analog ranging from 7.5 µg to 100 µg of vitamin D equivalent.

In some of these embodiments, the vaginal composition is comprised in a transmucosal delivery system or a vaginal ring, the said transmucosal delivery system or the said vaginal ring is placed in the vaginal cavity at defined periodicity and the vaginal composition is continuously released from the transmucosal delivery system or vaginal ring at a rate which is appropriate for releasing the combined estradiol and calcitriol at a daily dosage delivery of (i) estradiol ranging from 1 µg to 10 µg and (ii) calcitriol ranging from 0.25 µg to 1 µg.

In the embodiments of the method wherein the vaginal composition is comprised in a transmucosal delivery system or a vaginal ring, the said transmucosal delivery system or the said vaginal ring is placed in the vaginal cavity at defined periodicity and the vaginal composition is continuously released from the transmucosal delivery system or vaginal ring at a rate which is appropriate for releasing the combined estrogen and vitamin D or vitamin D analog at a daily dosage delivery of (i) estrogen ranging from 2 µg to 10 µg estrogen of estradiol equivalent and (ii) vitamin D or analog ranging from 7.5 µg to 100 µg of vitamin D equivalent.

In some of the embodiments of the method wherein the vaginal composition is comprised in a transmucosal delivery system or a vaginal ring, the said transmucosal delivery system or the said vaginal ring is placed in the vaginal cavity at defined periodicity and the vaginal composition is continuously released from the transmucosal delivery system or vaginal ring at a rate which is appropriate for releasing the combined estradiol and calcitriol at a daily dosage delivery of (i) estradiol ranging from 1 µg to 10 µg and (ii) calcitriol ranging from 0.25 µg to 1 µg of vitamin D equivalent.

Uses of the Vaginal Composition Disclosed herein

The invention further relates to the use of a composition comprising a combination of estrogen and vitamin D or vitamin D analog at a daily dosage delivery of (i) estrogen ranging from 1 µg to 100 µg estrogen of estradiol equivalent and (ii) vitamin D or analog ranging from 7.5 µg to 100 µg of vitamin D equivalent for treating vaginal atrophy.

In some embodiments, the daily dosage delivery of estrogen ranges from 1 µg to 70 µg.

In some embodiments, the daily dosage delivery of estrogen ranges from 1 µg to 10 µg.

The invention further relates to the use of a composition comprising a combination of estradiol and calcitriol at a daily dosage delivery of (i) estradiol ranging from 1 µg to 100 µg and (ii) calcitriol ranging from 0.075 µg to 1 µg as a vaginal pharmaceutical composition.

In some embodiments, the daily dosage delivery of estrogen ranges from 1 µg to 70 µg.

In some embodiments, the daily dosage delivery of estrogen ranges from 1 µg to 10 µg.

The invention further relates to the use of a composition comprising a combination of estradiol and calcitriol at a daily dosage delivery of (i) estradiol ranging from 1 µg to 100 µg and (ii) calcitriol ranging from 0.075 µg to 1 µg for treating vaginal atrophy.

In some embodiments, the daily dosage delivery of estrogen ranges from 1 µg to 10 µg.

EXAMPLES

Example 1: Evaluation of the Effect of a Combination of Estradiol and Vitamin D on Vaginal Atrophy in an Experimental Model of Menopause The effect of the combination of a low dose estrogen with a dose of vitamin D on vaginal atrophy is explored by using a recognized experimental model of menopause, namely in the experimental model of ovariectomized rodent, i.e. in ovariectomized rat and ovariectomized mouse.

A. Animal Model of Menopause and VVA: Ovariectomized Rodent (Rat or Mice)

Ovariectomized rat is an animal model of estrogen deficiency that has been used to evaluate vaginal effects of different products such as ospemifene or DHEA. Dose response of ospemifene in the rat was consistent with that observed in clinical studies, showing that this animal model is a highly predictive model of ospemifene activity in postmenopausal vulvovaginal atrophy (Unkila M et al., *J Steroid Biochem Mol Biol.* 2013 November; 138:107-15.). Vaginal effects of intravaginal application of DHEA has also been studied in this animal model (Berger L et al., *J Steroid Biochem Mol Biol.* 2008 March; 109(1-2):67-80. Berger L et al., *J Steroid Biochem Mol Biol.* 2005 Jul; 96(2):201-15.).

B. Markers of Vaginal Atrophy

Occurrence of vaginal atrophy as well as degree of vaginal atrophy shall be assessed through the use of a plurality of markers which are the following:
vaginal epithelium thickness and morphology after chronic treatment;
measurement of vaginal tissue wet weight as an index of tissue atrophy
measurement of vaginal pH, preferably by using a pH indicator strip before and after chronic treatment,
measurement of the vaginal maturation index (VMI), which measurement is performed on vaginal smears before and after chronic treatment.

C. Marker of Systemic Effect

Systemic effect of a local hormonal treatment shall be assessed by measurement of the uterus weight after chronic treatment.

C. Test Compositions

The ovules are prepared by using Ovucire® (Ref 3460-Gattefosse, France) as the starting material. Ovucire® material is a blend of semi-synthetic glycerides comprising a mixture of saturated $C_{12}$-$C_{18}$ triglyceride fatty acids and additives. More precisely, this starting material is a mixture of hard fat EP/NF/JPE (and) glyceryl ricinoleate (and) ethoxylated fatty alcohols (ceteth-20, steareth-20) EP/NF The melting point of Ovucire® is in the range of 32.5° C.-34.0° C. Ovucire® starting material is under the form of waxy solid pellets at temperature of the laboratory.

The ovules are prepared by using a conventional technique. Ovules are stored refrigerated until the time of their usage.

D. Experimentation Schedule 8-10 weeks-old female Sprague Dawley rats (Janvier, France) are first acclimated during a period of time of one week or more.

The acclimated rats undergo a bilateral ovariectomy (at "Day 0"), so as to induce an experimental menopause.

Three weeks after ovariectomy (at Day 21), the ovariectomized rats are divided in five distinct groups of at least eight animals per group, respectively:

Group 1: the ovariectomized rats receive no treatment at all

Group 2: the ovariectomized rats are administered once daily with an ovule comprising a liquid saline (placebo)

Group 3: the ovariectomized rats are administered once daily with an ovule comprising estradiol alone, in the absence of vitamin D analog Group 4: the ovariectomized rats are administered once daily with an ovule comprising vitamin D analog alone, in the absence of estradiol Group 5: the ovariectomized rats are administered once daily with an ovule comprising (i) the combination of estradiol and vitamin D analog.

Each of the Groups 1, 2, 3, 4 and 5 of ovariectomized rats receives the indicated treatment during a period of time of six weeks (thus until Day 63).

The body weight of each tested animal is monitored twice a week.

Vaginal pH of each tested animal is monitored the day before the first treatment, and in all cases the day following the last treatment (at Day 64).

Smears of vaginal tissue are collected from each of the tested animal by gentle scraping along the wall of the vagina the day before the first treatment and the day following the last treatment for determining the Vaginal Maturation Index (VMI).

At the end of the experiment (at Day 64), animals are sacrificed and the vagina and uterus are collected and their respective wet weight is determined.

One part of the vagina tissue material is paraffin-embedded. Slices of the paraffin-embedded vaginal tissue are stained for studying and measuring the vaginal epithelium thickness as well as the vaginal epithelium morphology.

One part of the vagina tissue material is rapidly stored at −80° C. for further experiment.

E. Doses

The median local estradiol dose has been calculated from the minimal marketed daily dose effective in women, namely 7.5 µg. Dosing was calculated utilizing weight-based comparisons with human dosage as previously published in similar studies (Montoya T I et al., 2015; Biol Reprod.;92 (2):43). The dose in a 70 kg women delivers 7.5 µg. By weight comparison, this translates into 0.11 µg/kg, and consequently into a 0.043 µg estradiol dose in a 400 g animal.

The minimum estradiol dose has been calculated by the same method from 2 µg in women; by weight comparison, this translates into 0.01 µg estradiol dose in a 400 g animal.

According to animal response to treatment a 10-fold higher dose than the median dose could be the maximum estradiol dose. This translates into 0.4 µg in a 400 g animal.

Dose of estradiol tested in animals is selected in the range of 0.01 µg to 0.4 µg estradiol dose in a 400 g animal.

The dose of calcitriol has been calculated by the same method. The dose of calcitriol chosen in women is 0.075 µg to 1.00 µg. By weight comparison, this translates into 0.0004 µg to 0.006 µg.

E. Measures

The following parameters are used for characterizing the status of the vaginal epithelium in each of the groups 1 to 5 of animals tested:
vaginal epithelium thickness,
vaginal pH value before and after chronic treatment.
vaginal tissue wet weight after chronic treatment.
vaginal maturation index (VMI), which measurement is performed on vaginal smears before and after chronic treatment.

E.1. Measures Performed on the Vaginal and Uterine Tissues

The day following the last treatment, the rats are anesthetized with an overdose of urethane to:
measure vaginal pH using a pH-indicator strip (3 readings/rot)
collect a vaginal smear for VMI assessment (2 samples/rat).
harvest vaginal/uterine horns.
After cleaning the vaginal and uterus tissues:
vaginal tissue is weighed to obtain wet weight as an index of tissue atrophy.
uterine horns are weighed to rule out (or not) a systemic effect of the local treatment, either by placebo, estradiol, vitamin D or the combination of estradiol and vitamin D.
Vaginal tissue is then separated into two parts:
one half is fixed in 10% neutral buffered formalin and paraffin-embedded for epithelium thickness evaluation and morphology (H&E coloration)
the second half will be immediately frozen and stored at −80° C. for further evaluation.

E.2. Vaginal Maturation Index (VMI) Assessment

For each rat, 2 samples are taken by gentle scraping along the wall of the vagina.

Then, each sample is smeared on one slide and fixed using a special cytology fixative (labofix-VWR ref 13356770).

Papanicolaou stain (RAL diagnostics) is performed to assess a VMI.

VMI is assessed as a ratio obtained through performing a random count of 3 major cell types. VMI=% leucocytes, % nucleated cells, % cornified cells.

Predominance of leukocytes indicates vaginal atrophy (absence of estrogen stimulation) and predominance of nucleated and cornified cells indicates effectiveness of supplementation: Nucleated cells comprise parabasal cells and intermediate cells. Cornified cells consist of the superficial cells.

Cell counts are performed by digital slide scanning and image analysis, using an Aperio® AT2 apparatus marketed by the company Leica Biosystems (Germany), according to the following protocol:

analyzing images of 5 sections per slide (×40) will be used for analysis. Thus, for each rat, a total of 10 sections will be reviewed for VMI assessment.

E.3. Epithelium Thickness Evaluation

Vaginal tissue is embedded in paraffin, sectioned and stained with hematoxylin/eosine (2 slides/rat) using a fully automated multi-stainer system for histological analysis, the Multistainer ST5020 in conjunction with the CV5030 Coverslipper marketed by the Company Leica Biosystems (Germany).

Digital slide scanning and image analysis for Vaginal epithelial thickness evaluation is performed according to the following protocol:

3 sections/slide: the first 2 sections (5 fields/section) of each slide is used for analysis. The $3^{rd}$ section is considered as a back-up section. Thus, for each rat, a total of 20 fields is reviewed for histo-morphometry.

F. Comments on the Experimental Results

Overall, the rats reacted well to the various treatment conditions tested, as it was confirmed by the regular body weight increase. As it is shown in FIG. 1, treatment conditions with estradiol, calcitriol or combination of estradiol and calcitriol, irrespective of the dose of estradiol or calcitriol that were used, did not cause any change in the animal body weight. The results depicted in FIG. 1 showed that no significant difference in body weight evolution among the different experimental groups was observed at the end of the treatment time period.

Further, the results showed no difference in the vaginal pH value of the animals at the start of the experiment, nor a vaginal pH value difference at the end of the treatment time period. This is probably due to the low sensitivity of pH-indicator strips to detect small variability or to the large interindividual variability.

Figure 2:
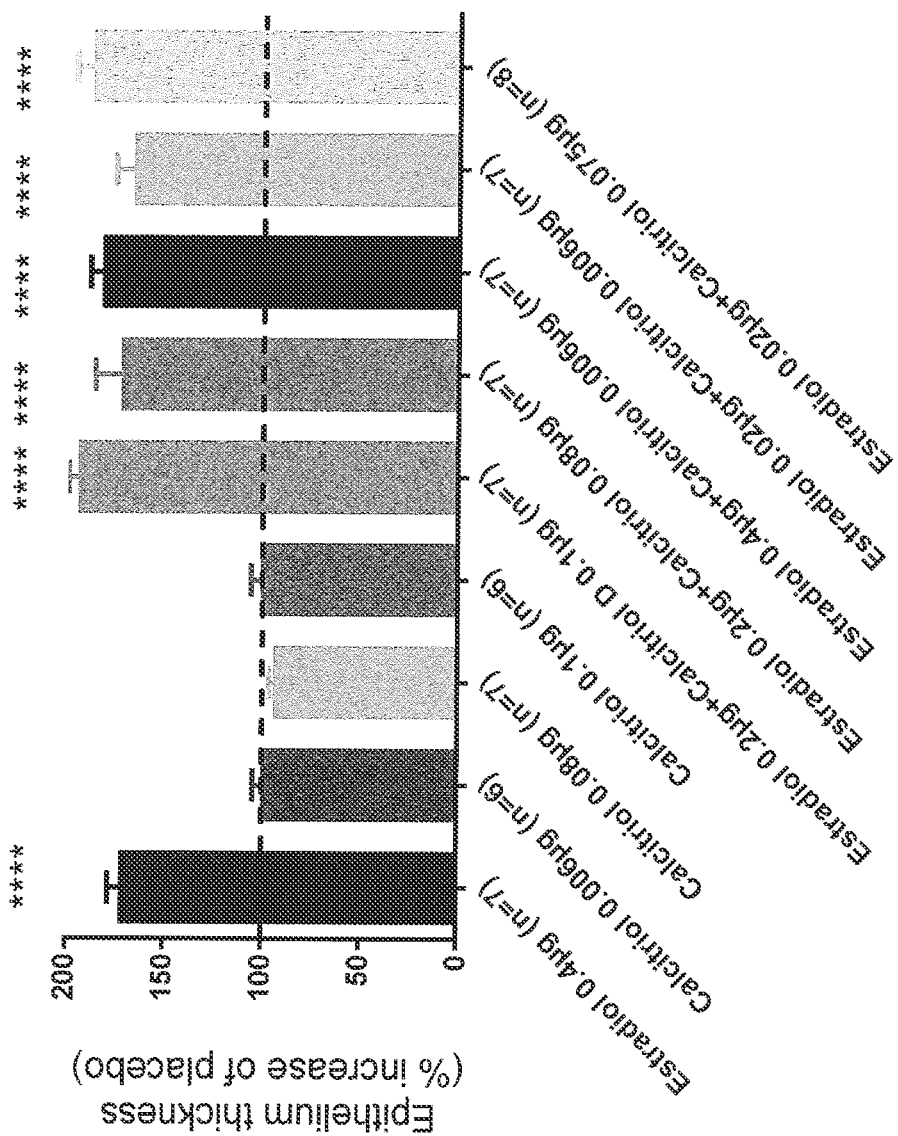
FIG. 2 illustrates a graph of the epithelium thickness. The epithelium thickness values are reported as the percentage of increase as compared with the placebo conditions following a 6-week treatment period for each of the experimental groups. Ordinate: epithelium thickness, as expresses in percentage increase versus placebo. Bars from the left to the right of FIG. 2: Estradiol 0.4 µg (n=7); Calcitriol 0.006 µg (n=6); Calcitriol 0.08 µg (n=7); Calcitriol 0.1 µg (n=6); Estradiol 0.2 µg+Calcitriol 0.1 µg (n=7); Estradiol 0.2 µg+Calcitriol 0.08 µg (n=7); Estradiol 0.4 µg+Calcitriol 0.006 µg (n=7); Estradiol 0.02 µg+Calcitriol 0.006 µg (n=7); Estradiol 0.02 µg+0.075 µg (n=8). Data are represented as the mean value+/− SEM. "**" means p<0.0001 versus placebo conditions using the Dunnett's multiple comparisons post-hoc test through the one-way ANOVA test. Dashed line: mean epithelium thickness value of the animal group that has received placebo.

Epithelium thickness was measured as it directly illustrates the effect of a given treatment on vaginal atrophy. As shown in FIG. 2, a 0.4 µg dose of estradiol induces a high increase in the vaginal epithelium thickness, as compared to placebo (the dashed line in FIG. 2). Calcitriol alone, irrespective of the dose which has been tested, did not cause any change in the vaginal epithelium thickness. However, when a low dose of estradiol was combined to a non-active dose of calcitriol, a substantial increase in the vaginal epithelium thickness was observed. FIG. 2 shows that the combination of low combination doses such as 0.02 µg estradiol with 0.006 µg calcitriol cause an increase in the vaginal epithelium thickness that is of the same order than a twenty fold higher dose of estradiol alone. At the dose of 0.02 µg estradiol, that is administered locally, there is a reduced risk of systemic passage of biologically active amounts of estradiol. Especially, at the dose of 0.02 µg of local administration of estradiol, systemic adverse effects are avoided or at least considerably reduced. Almost the same remarks may be made regarding the 0.2 µg estradiol combination treatment conditions, although the risk of systemic activity may be increased.

Regarding the assessment of the Vaginal Maturation Index (VMI), beyond the vaginal epithelium thickness, an important parameter resides in the cellular constitution of the vaginal epithelium, which includes the content of the vaginal epithelium in cornified cells and leukocytes, respectively.

Figure 3A:
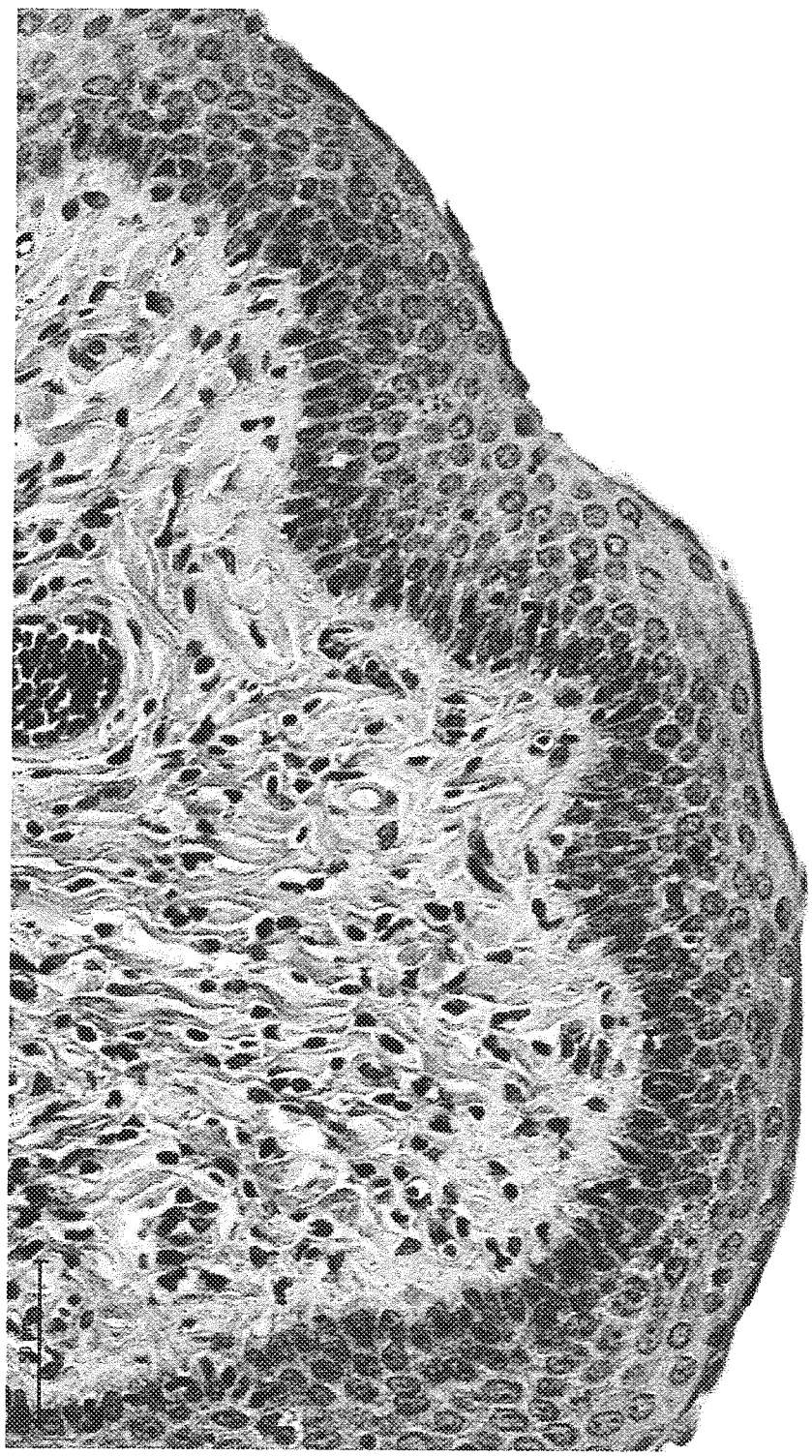
FIG. 3 illustrates photographs of histological vaginal tissue slices (i) in placebo experimental conditions (FIG. 3A), (ii) animals treated with 0.02 µg estradiol (FIG. 3B), (iii) animals treated with 0.08 µg estradiol (FIG. 3C) and (iv) animals treated with 0.4 µg estradiol (FIG. 3D).
Figure 3B:
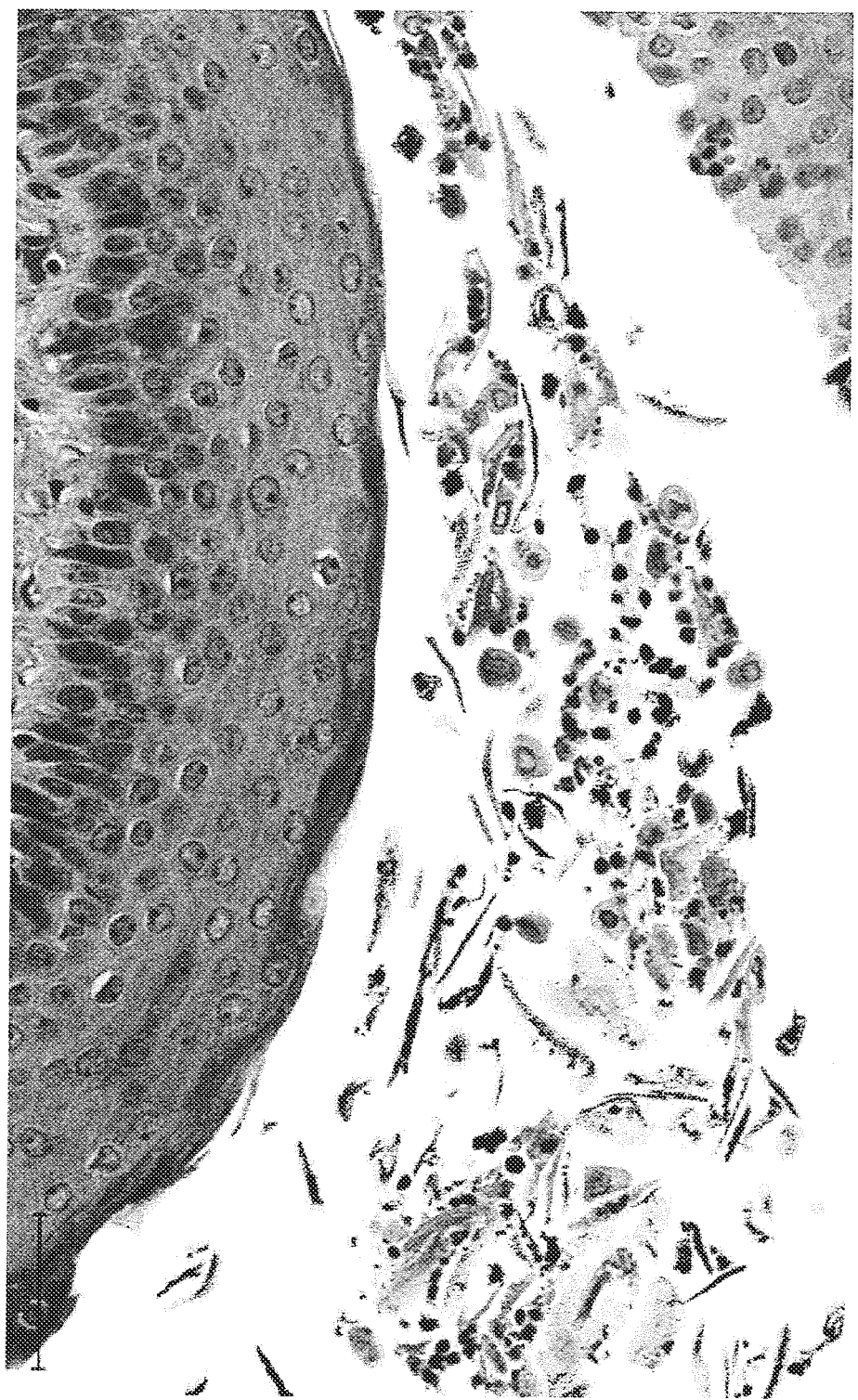
Figure 3C:
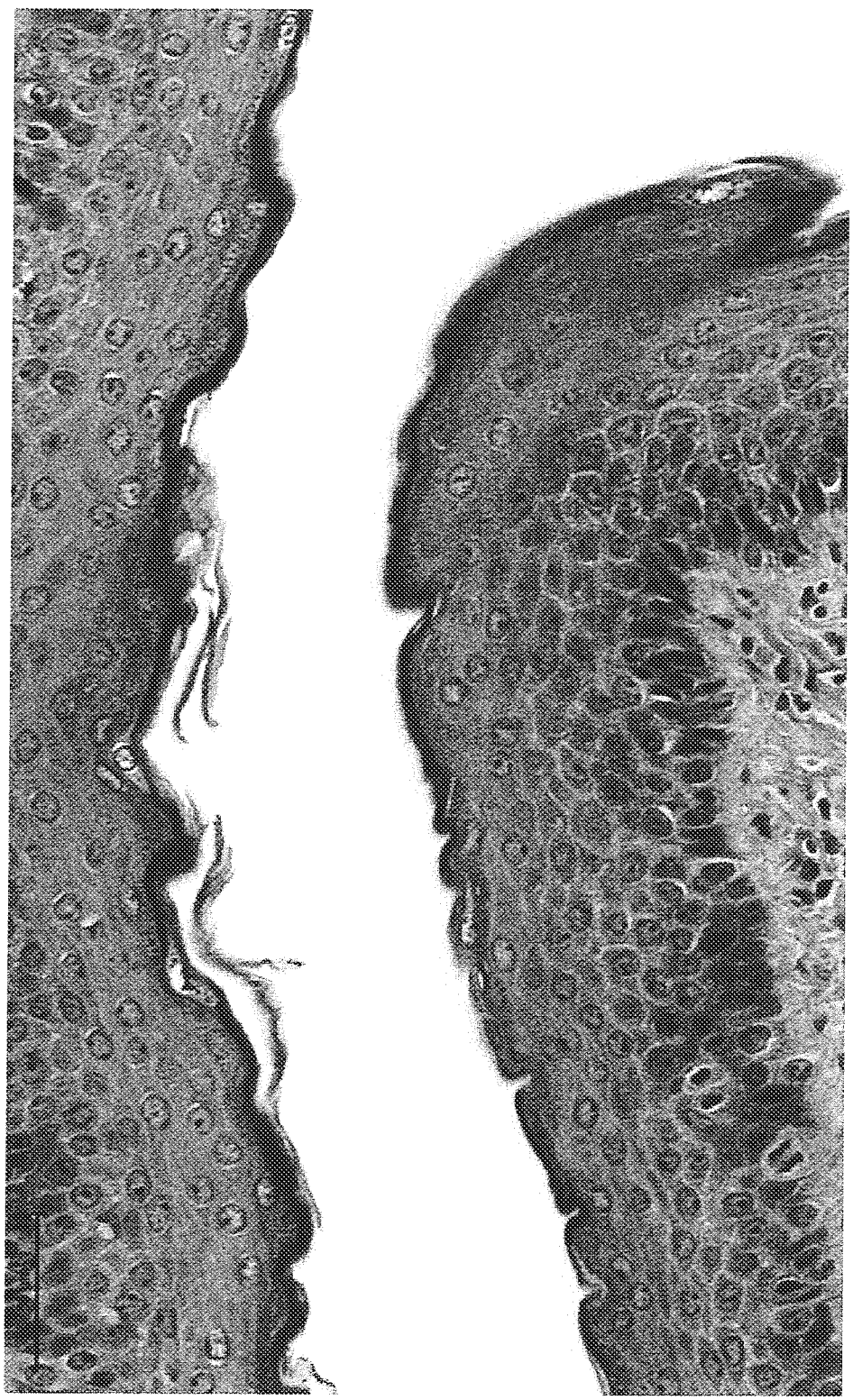
Figure 3D:
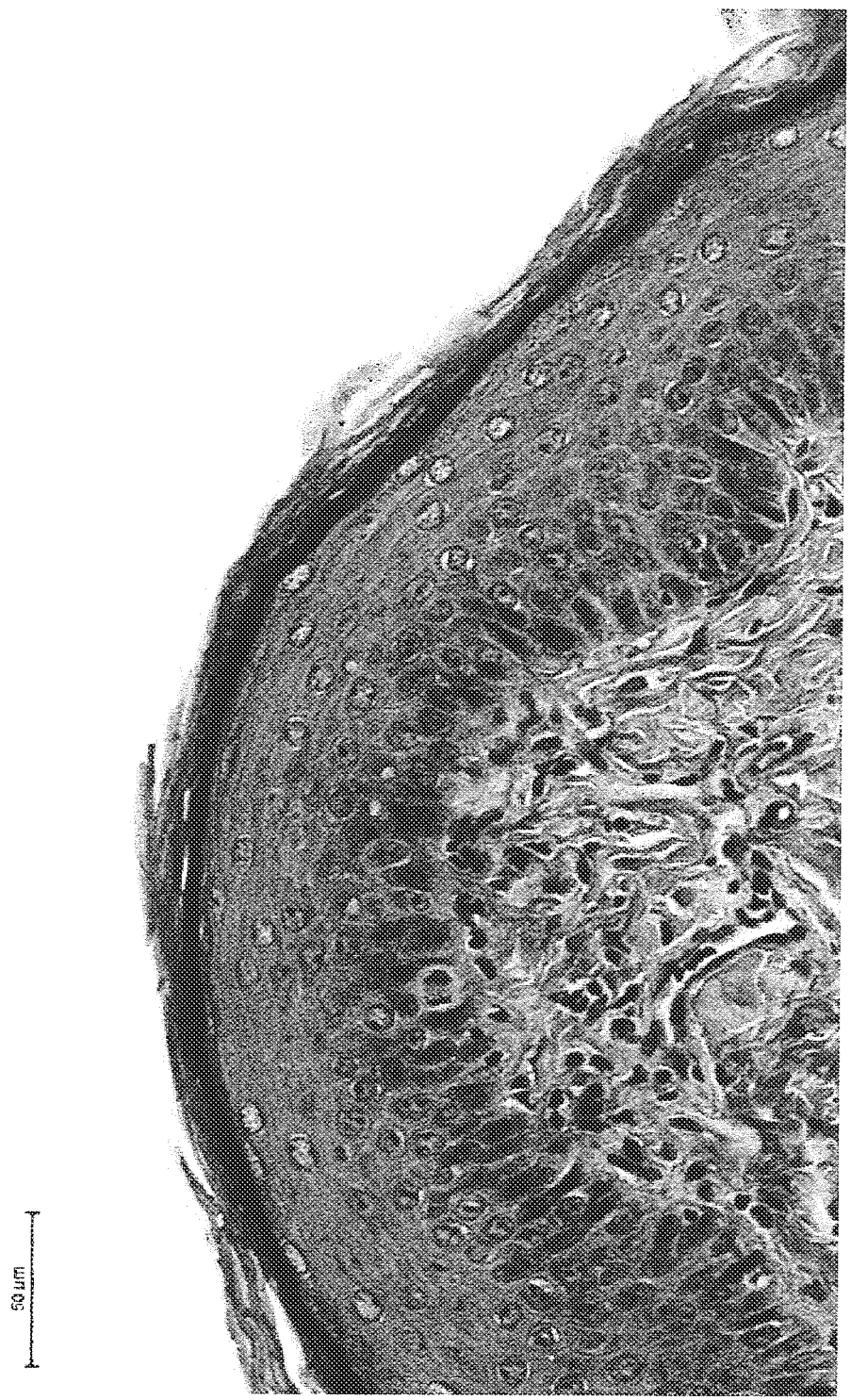
Figure 4:
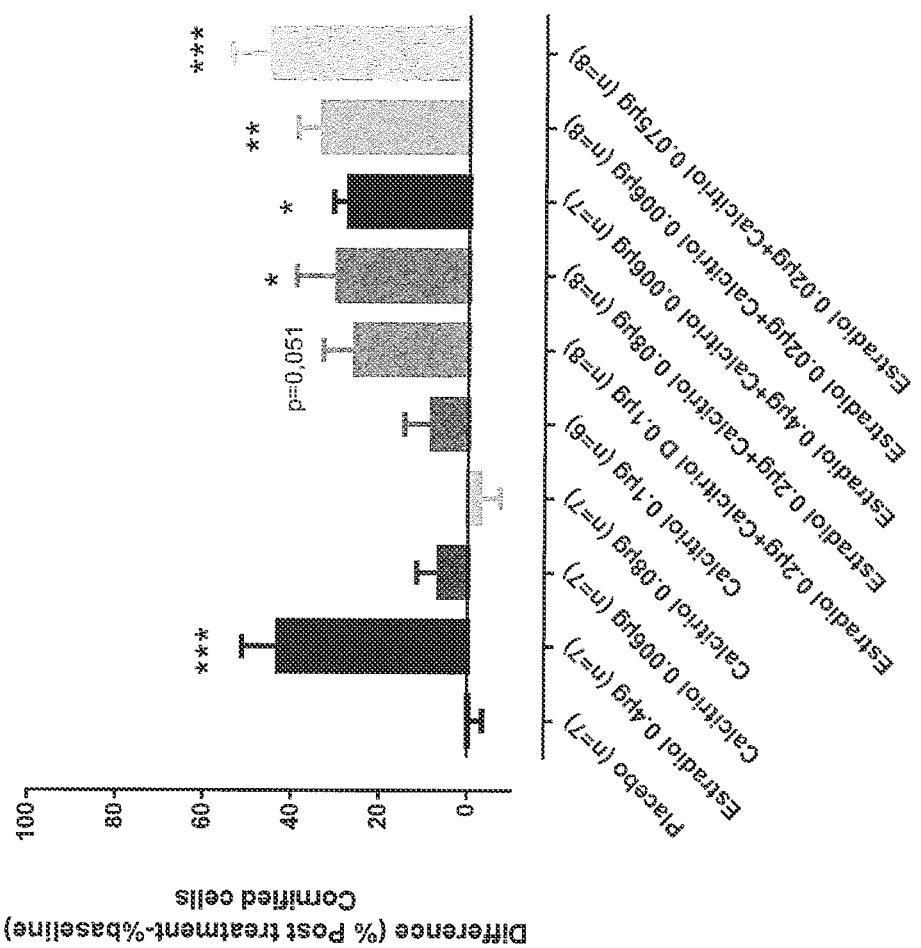
FIG. 4 illustrates the effect of the various treatment conditions on the maturation status of the vaginal tissue, as illustrated by the percentage of cornified cells. Data (ordinate values) are presented as the change from the baseline in the percentage of cornified cells following a 6-week treatment period. Data are presented as the mean values +/− SEM. "*" means p<0.05; "" means p<0.01; "*" means p<0.001. Statistical significance was determined by using Dunnett's multiple comparisons post-hoc test following one-way ANOVA test. Bars form the left to the right of the FIG. 4: Placebo (n=7); Estradiol 0.4 µg ("***"; n=7); Calcitriol 0.006 µg (n=7); Calcitriol 0.08 µg (n=7); Calcitriol 0.1 µg (n=6); Estradiol 0.2 µg+Calcitriol 0.1 µg (p=0.051; n=8); Estradiol 0.2 µg+Calcitriol 0.08 µg ("*"; n=8); Estradiol 0.4 µg+Calcitriol 0.006 µg ("*"; n=7); Estradiol 0.02 µg+Calcitriol 0.006 µg (""; n=8); Estradiol 0.02 µg+Calcitriol 0.075 µg ("*"; n=8).

As regards the vaginal epithelium cornified cells layer, FIG. 3A illustrates a histological view of the vaginal epithelium of an ovariectomized rat having received locally placebo-containing ovules only. FIG. 3A shows the *stratum germinativum* which is composed of *stratum basale* as a single layer of columnar cells and outer *stratum spinosum* (the darker external cell layer in FIG. 3A) as multiple layers of polyhedral cells. The cornified cells layer locates us the thin and discontinuous extreme outer cell layer in FIG. 3A. The histological photograph of FIG. 3B shows that a 0.02 µg dose of estradiol does not cause a detectable change in the cornified cell layer, whereas the histological photographs of FIGS. 3C and 3D illustrate that the cornified cell layer have a thickness and a density which increase with the increasing doses of 0.08 µg and 0.4 µg estradiol.

Further, the results depicted in FIG. 3 show that although calcitriol induced no significant change in the content of the vaginal epithelium cornified cells, irrespectively of the doses which were tested, even the combination of the lowest doses of estradiol and calcitriol, respectively, causes a high increase in the cornified cells content, which denotes a highly positive effect on the maturation of the vaginal epithelium, i.e. a recovery of the mature vaginal epithelium structure, and thus a recovery from the experimentally-induced vaginal atrophy.

Figure 5:
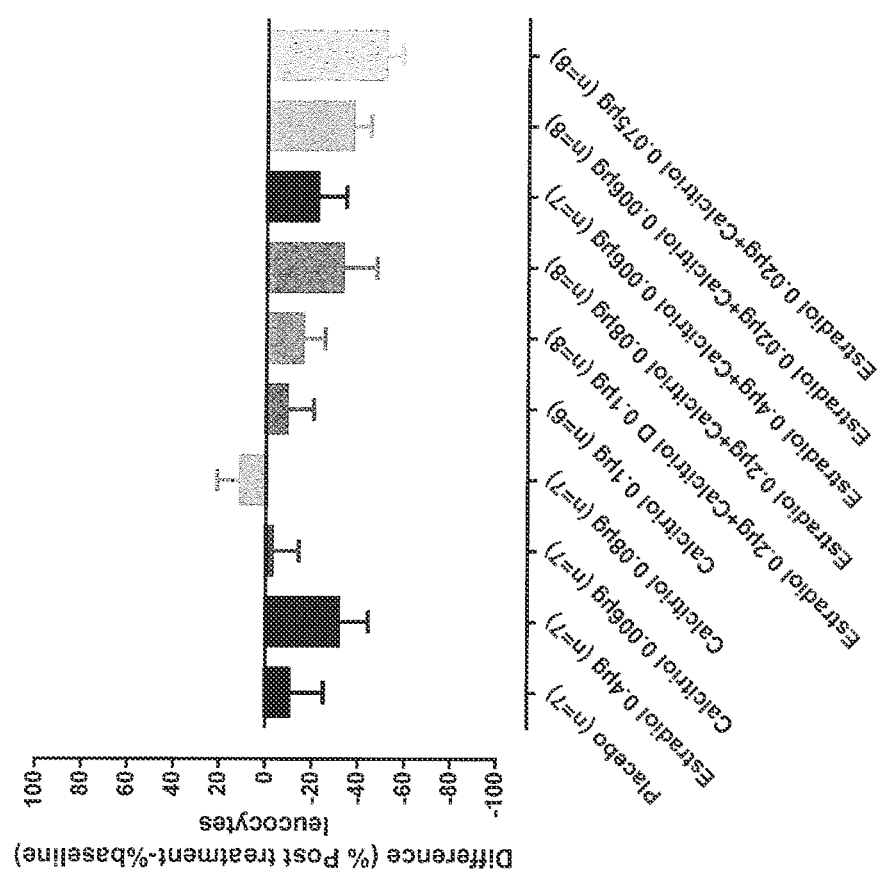
FIG. 5 illustrates a graph depicting the effect of the various treatment conditions on the maturation status of the vaginal tissue, as illustrated by the percentage of leukocytes. Data (ordinate values) are presented as the change from the baseline in the percentage of cornified cells following a 6-week treatment period. Data are presented as the mean values +/− SEM. "*" means p<0.05. Statistical significance was determined by using Dunnett's multiple comparisons post-hoc test following one-way ANOVA test. Bars form the left to the right of the FIG. 4: Placebo (n=7); Estradiol 0.4 µg (n=7); Calcitriol 0.006 µg (n=7); Calcitriol 0.08 µg (n=7); Calcitriol 0.1 µg (n=6); Estradiol 0.2 µg+Calcitriol 0.1 µg (n=8); Estradiol 0.2 µg+Calcitriol 0.08 µg (n=8); Estradiol 0.4 µg+Calcitriol 0.006 µg (n=7); Estradiol 0.02 µg+Calcitriol 0.006 µg (n=8); Estradiol 0.02 µg+Calcitriol 0.075 µg (n=8).

As shown in FIG. 5, the combination of very low doses of 0.02 µg estradiol and 0.006 µg calcitriol, thus at doses wherein calcitriol alone causes no effect, causes a high decrease in the vaginal epithelium content in leukocytes, which is another result confirming that the combination treatments tested reversed the experimentally-induced vaginal atrophy.

Figure 6:
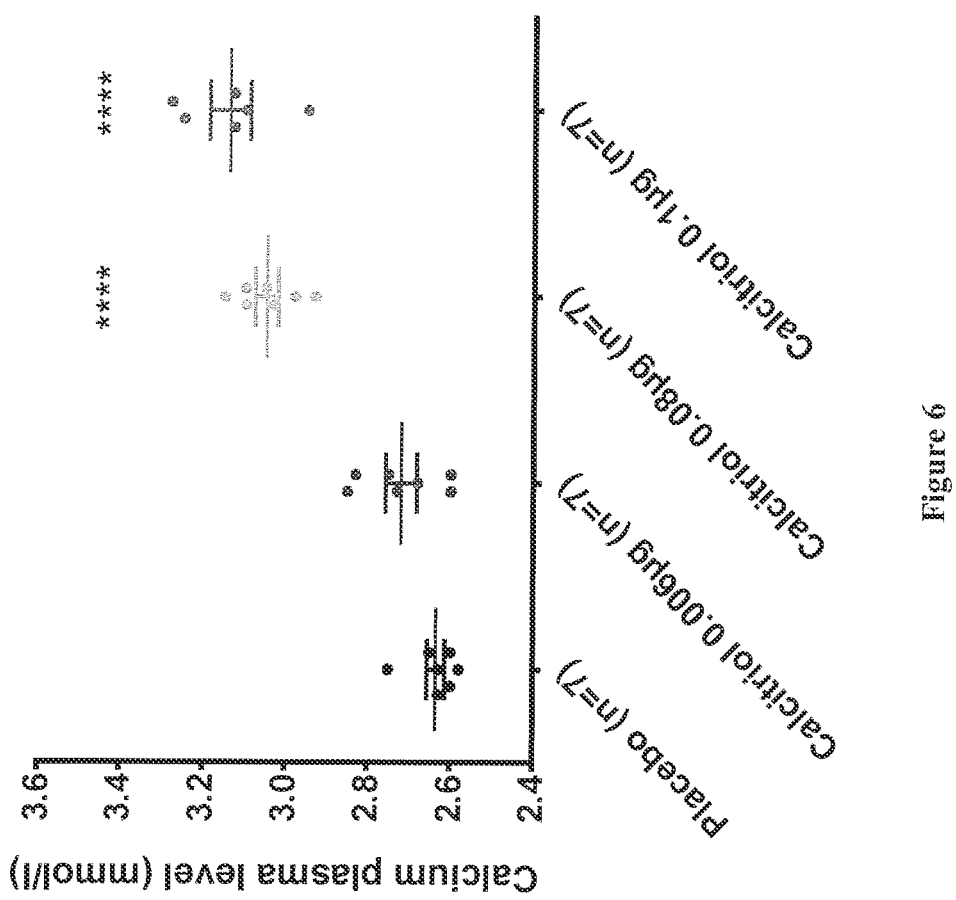
FIG. 6 illustrates the calcium plasma level in the various treatment conditions. Ordinate: calcium plasma level values, as expressed as mmol/L. From the left to the right of FIG. 6: Placebo (n=7); Calcitriol 0.006 µg (n=7); Calcitriol 0.08 µg ("**"; n=7); Calcitriol 0.1 µg (""; n=7). Data are presented as the mean values +/− SEM. "**" means p<0.001 versus placebo. Statistical significance was determined by using Dunnett's multiple comparisons post-hoc test following one-way ANOVA test.

Also, as shown in FIG. 6, the calcium plasma level was significantly increased at the doses of 0.08 µg and 0.1 µg, respectively.

However, it may be noticed that the use of calcitriol dose as low as 0.006 µg did not cause any significant change in the calcium plasma level.

Altogether, the results presented in this example show the effectiveness of the combination of estradiol and calcitriol at low doses for treating vaginal atrophy.

It may be added that at certain low dose ranges of the combined treatment, the said combined treatment may allow substantially avoiding undesirable side effects, such as (i) significant systemic presence of estradiol and (ii) plasma calcium level increase.

The invention claimed is:
1. A vaginal composition comprising, as active ingredients, a combination consisting of estrogen and vitamin D or a vitamin D analog at a daily dosage delivery of (i) estrogen ranging from 1 µg to 10 µg estrogen of estradiol equivalent and (ii) vitamin D or analog ranging from 7.5 µg to 100 µg of vitamin D equivalent.

2. The vaginal composition according to claim 1, wherein the daily dosage delivery of estrogen ranges from 1 µg to 7.5 µg of estradiol equivalent.

3. The vaginal composition according to claim 1 wherein the said composition has a liquid, solid or semi-solid presentation.

4. The vaginal composition according to claim 1 wherein said vaginal composition is a cream or a gel composition.

5. The vaginal composition according to claim 1 presented as daily unit dosage form of a suppository.

6. The vaginal composition according to claim 5, wherein the suppository is selected from a group consisting of a capsule, an ovule and a tablet.

7. The vaginal composition according to claim 1 which is comprised in a delivery device selected from the group consisting of a transmucosal device and a vaginal ring.

8. The vaginal composition according to claim 1 wherein the said estrogen is selected from the group consisting of estradiol, estradiol valerate, estradiol benzoate, estradiol 17β-cypionate, estradiol dipropionate, estradiol enanthate, estropipate, equilenin, equilin, estriol, estriol succinate, estrone, ethinyl estradiol, estetrol, quinestrol, quinestranol, conjugated estrogens, esterified estrogens, and mixtures thereof.

9. The vaginal composition according to claim 1 wherein the said estrogen is estradiol or a derivative thereof.

10. The vaginal composition according to claim 1 wherein the vitamin D analog is selected from the group consisting of cholecalciferol, ergocalciferol, paricalcitol, doxercalciferol, dihydrotachysterol and derivatives thereof.

11. The vaginal composition according to claim 1, wherein the vitamin D analog is selected from the group consisting of calcitriol and calcipotriol.

12. A method for treating vaginal atrophy in a subject, comprising providing to a vagina of the subject as active ingredients a combination consisting of estrogen and vitamin D or vitamin D analog at a daily dosage delivery of (i) estrogen ranging from 1 µg to 10 µg estrogen of estradiol equivalent and (ii) vitamin D or analog ranging from 7.5 µg to 100 µg of vitamin D equivalent.

13. The method of claim 12, wherein the daily dosage delivery of estrogen ranges from 1 µg to 7.5 µg of estradiol equivalent.

14. A method for treating vaginal atrophy in a subject, comprising providing to a vagina of the subject as active ingredients a combination consisting of estradiol and calcitriol at a daily dosage delivery of (i) estradiol ranging from 1 µg to 10 µg and (ii) calcitriol ranging from 0.075 µg to 1 µg.

15. The vaginal composition according to claim 1, wherein the daily dosage delivery of estrogen ranges from 1 µg to 7.5 µg of estradiol equivalent and said composition is a vaginal tablet.

16. The method according to claim 12, wherein the daily dosage delivery of estrogen ranges from 1 µg to 7.5 µg of estradiol equivalent and said composition is a vaginal tablet.

17. The method according to claim 14, wherein the daily dosage delivery of estradiol ranges from 1 µg to 7.5 µg and said composition is a vaginal tablet.

18. The method of claim 16, wherein the daily dosage delivery of estrogen ranges from 1 µg to 7.5 µg of estradiol equivalent.

* * * * *